United States Patent [19]

Tomalski et al.

[11] Patent Number: 5,266,317

[45] Date of Patent: Nov. 30, 1993

[54] INSECT-SPECIFIC PARALYTIC NEUROTOXIN GENES FOR USE IN BIOLOGICAL INSECT CONTROL: METHODS AND COMPOSITIONS

[75] Inventors: Michael D. Tomalski; Lois K. Miller, both of Athens, Ga.

[73] Assignee: University of Georgia Research Foundation, Inc., Athens, Ga.

[21] Appl. No.: 593,657

[22] Filed: Oct. 4, 1990

[51] Int. Cl.[5] .................. C12N 7/01; C12N 15/12
[52] U.S. Cl. ..................... 424/93 T; 536/23.5; 435/235.1; 435/69.1; 435/172.3; 435/320.1
[58] Field of Search ............. 536/27, 93.5; 935/36; 435/69.1, 235.1, 320.1, 172.3; 424/93; 434/93 T

[56] References Cited

U.S. PATENT DOCUMENTS

| | | | |
|---|---|---|---|
| 4,394,443 | 7/1983 | Weissman et al. | 435/6 |
| 4,745,051 | 5/1988 | Smith et al. | 435/69.51 |
| 4,879,236 | 11/1989 | Smith et al. | 435/320.1 |
| 5,004,687 | 4/1991 | Miller | 435/69.1 |
| 5,041,379 | 8/1991 | Fraser et al. | 435/235.1 |

FOREIGN PATENT DOCUMENTS 2005658  6/1990  Canada .
0374753  6/1990  European Pat. Off. .

OTHER PUBLICATIONS

Dee et al. (1990) Bio/Technology 8:339-342.
Carbonell et al. (1988) Gene 73:409-418.
Maeda et al. (1989) Biochem. Biophys. Res. Comm. 165:1177-1183.
Zlotkin et al. (1985) Arch. Biochem. Biophys. 240:877-887.
Zlotkin (1987) Endeavor 11:168-174.
Dialog Abstract, published Jun. 1990 for EP 374753.
Tomalski et al. (1989) Toxicon 27:1151-1167.
Tomalski et al. (1988) Toxicon 26:127-132.
Miller et al. (1987) "Biotechnology in Invertebrate Pathology and Cell Culture" pp. 295-303.
Merryweather et al. (1990) J. Gen. Virol. 71:1535-1544.
Zlotkin et al. (1983) Comprehensive Insect Physiology Biochemistry and Pharmacology vol. 10 pp. 499-546.
Ooi et al. (1989) J. Mol. Biol. 210:721-736.
Rankin et al. (1988) Gene 70:39-49.
Crawford et al. (1988) J. Virol. 62:2773-2781.
Thiem et al. (1990) Gene 91:87-95.
Carbonell et al. (1985) J. Virol. 56:153-160.
Tomalski et al. (1986) Doctoral Thesis pp. vii-viii, 17-26, 29, 52-71, 92-95 102 and 105.
Sambrook et al. 1989. *Molecular Cloning: A Laboratory Manual*, Cold Spring Harbor Laboratory Press, pp. 8.47 and 11.57.
Watson, James D. 1987. *Molecular Biology of the Gene*, The Benjamin/Cummings Publishing Co. Inc., Menlo Park, Calif. p. 313.
Mullii et al. 1986. Cold Spring Harbor Symposia en Quantitative Biology, vol. 51, pp. 263-273.
Lathe, R. 1985. J. Mol. Biol., 183:1-12.
Pongor, S. 1987. Methods in Enzymology, 154:450-473.
Creighton, T. E. 1983. Protein & Structure and Molecular Principles. W. H. Freeman and Company, New York, pp. 93-98.
Van Brunt, J. 1989. Bio/Technology 7:324-325.
Berent et al. 1985. BioTechniques, May/Jun., pp. 208-220.
Lerner, R. A. 1982. Nature 299:592-596.
Doolittle, R. 1987. *Of URFs and ORFs*, University Science Books, Mill Valley, Calif., pp. 35 and 36.
Bougis et al. 1988. Proc. World Congr. Amim. Nat. Toxins, Jul. 31-Aug. 5, pp. 94-101.

*Primary Examiner*—Robert A. Wax
*Assistant Examiner*—Keith C. Furman
*Attorney, Agent, or Firm*—Greenlee and Winner

[57] ABSTRACT

Genes encoding insect-specific paralytic neurotoxins, particularly those of insect-parasitic mites, including Pyemotes, are described. Recombinant DNA molecules in which the neurotoxin coding sequences are placed under the control of heterologous promoters are also described. Such molecules are useful for the development of biological insect control agents which produce insect-toxic levels of the neurotoxin. Specifically described are genetically altered baculoviruses which produce insect-specific paralytic neurotoxins and which display improved toxic effect on insects. Insect-toxic compositions are also provided. Methods of insect control using these neurotoxin genes, methods for production of neurotoxins in cells, and methods of production of insect control agents are described.

61 Claims, 9 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:1:

Asp Asn Gly Asn Val Glu Ser Val Arg Ala Val Val Ile Asp Tyr Xaa
1               5                   10                  15

Asp Ile Arg His Pro
        20

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:2:

GGATCCGTTA ATTTAATAAT CTTATTTAC                       29

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:3:

GGATTTTAAC CTTGACATAC ATCTG                            25

(2) INFORMATION FOR SEQ ID NO:4:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (i i) MOLECULE TYPE: cDNA to mRNA (i x) FEATURE:
        (A) NAME/KEY: CDS
        (B) LOCATION: 12..884

(i x) FEATURE:
        (A) NAME/KEY: matpeptide
        (B) LOCATION: 129..884

(x i) SEQUENCE DESCRIPTION: SEQ ID NO:4:

```
CTTATTAATT A ATG AAA ATT TGT ACA TTT TTT ATT CCT TTA TTC AAA ATG        50
             Met Lys Ile Cys Thr Phe Phe Ile Pro Leu Phe Lys Met
             -39             -35                 -30

AAC TTG TTT TTT TTA TTT ATT ATT CCA ACA ATT TTA GCA GTT AAA CCT         98
Asn Leu Phe Phe Leu Phe Ile Ile Pro Thr Ile Leu Ala Val Lys Pro
    -25                 -20                 -15

TTT AGG TCT TTT AAT AAT ATT TCC TTA ATT GAT AAT GGC AAT GTC GAA        146
Phe Arg Ser Phe Asn Asn Ile Ser Leu Ile Asp Asn Gly Asn Val Glu
-10                  -5                   1                   5

TCT GTA AGA GCA GTA GTT ATT GAT TAT TGT GAT ATT AGA CAT CCA AAT        194
Ser Val Arg Ala Val Val Ile Asp Tyr Cys Asp Ile Arg His Pro Asn
            10                  15                  20

AAT TTA TGT AAA AAA CAT TTT GAA ATC GAT TCA TAT TGG AAT GAT GAT        242
Asn Leu Cys Lys Lys His Phe Glu Ile Asp Ser Tyr Trp Asn Asp Asp
        25                  30                  35
```

```
ACG GAT TGT TTT ACA AAT ATT GGA TGC AAA GTA TAT GGA GGA TTT GAT          290
Thr Asp Cys Phe Thr Asn Ile Gly Cys Lys Val Tyr Gly Gly Phe Asp
    40              45              50

ATT ATT GGT GGT CAT ACC CCT AAA GTT GGA ACT GTA TGT AGA CTT AAA          338
Ile Ile Gly Gly His Thr Pro Lys Val Gly Thr Val Cys Arg Leu Lys
55              60              65              70

AAA GGA GAA AAT AAA TTT GGA TAT TGT AAT TCA AAG GGA AAT TGC GTT          386
Lys Gly Glu Asn Lys Phe Gly Tyr Cys Asn Ser Lys Gly Asn Cys Val
                75              80              85

GAA AGA GAT TTT AAA GAA AGT TTT GGA ATA TCT ATA AAA ATA AAA GGA          434
Glu Arg Asp Phe Lys Glu Ser Phe Gly Ile Ser Ile Lys Ile Lys Gly
            90              95              100

ATT TCT AAT AAA GGA GAT GAT GAA CCA GCA TGT CCA CAA TAT AAA AAT          482
Ile Ser Asn Lys Gly Asp Asp Glu Pro Ala Cys Pro Gln Tyr Lys Asn
        105             110             115

ACT TGG ATT AAT TAT GGG AAA TGT AAT GAA CCT TAT TAT TGT GGA ACA          530
Thr Trp Ile Asn Tyr Gly Lys Cys Asn Glu Pro Tyr Tyr Cys Gly Thr
120             125             130

AAT CAT GGA TTA TTT TAT GCA AAC AAA AGA AAA CTC GAT TAC TTT CCC          578
Asn His Gly Leu Phe Tyr Ala Asn Lys Arg Lys Leu Asp Tyr Phe Pro
135             140             145             150

ACA GAC GGT GAA AAA TGT AAT TCA AAT AAT ATA CCA TAT GCT GTT TGT          626
Thr Asp Gly Glu Lys Cys Asn Ser Asn Asn Ile Pro Tyr Ala Val Cys
                155             160             165

TAT TTA GGA AGA TGT CAT ACA ACA GGT GGT TTT TTT AGT GAA TTT GGA          674
Tyr Leu Gly Arg Cys His Thr Thr Gly Gly Phe Phe Ser Glu Phe Gly
            170             175             180

ACT ATT GTT AAA AAT GTC GAA ATC GTA ACT TTA TCA GAT GGA AAG AAC          722
Thr Ile Val Lys Asn Val Glu Ile Val Thr Leu Ser Asp Gly Lys Asn
        185             190             195

AGT TCT AGA AGA GGA AAA CAT AAA AAT TTA CCT ACT TCT AAA GTA TTT          770
Ser Ser Arg Arg Gly Lys His Lys Asn Leu Pro Thr Ser Lys Val Phe
200             205             210

GAT AGT TAT AGT ATA TAT GAT ATT GAT CCT AAA AAT TGG AAA ATT GAA          818
Asp Ser Tyr Ser Ile Tyr Asp Ile Asp Pro Lys Asn Trp Lys Ile Glu
215             220             225             230

GAT GAT GAT AAA GAT GTT ACT GTT CAT GAA AAT ACA TTA GAT CCA AAA          866
Asp Asp Asp Lys Asp Val Thr Val His Glu Asn Thr Leu Asp Pro Lys
                235             240             245

AGT GAT TCA AGA CTG TGT TAAATTTTTA AAAATTTGAT TTTTTTAAAT                 914
Ser Asp Ser Arg Leu Cys
            250

AAATGTCAAT                                                               924
```

( 2 ) INFORMATION FOR SEQ ID NO:5:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Lys Ile Cys Thr Phe Phe Ile Pro Leu Phe Lys Met Asn Leu Phe
-39             -35             -30             -25

Phe Leu Phe Ile Ile Pro Thr Ile Leu Ala Val Lys Pro Phe Arg Ser
            -20             -15             -10

Phe Asn Asn Ile Ser Leu Ile Asp Asn Gly Asn Val Glu Ser Val Arg
        -5              1               5

Ala Val Val Ile Asp Tyr Cys Asp Ile Arg His Pro Asn Asn Leu Cys
10              15              20              25
```

```
Lys  Lys  His  Phe  Glu  Ile  Asp  Ser  Tyr  Trp  Asn  Asp  Asp  Thr  Asp  Cys
               30                  35                       40

Phe  Thr  Asn  Ile  Gly  Cys  Lys  Val  Tyr  Gly  Gly  Phe  Asp  Ile  Ile  Gly
                    45                  50                       55

Gly  His  Thr  Pro  Lys  Val  Gly  Thr  Val  Cys  Arg  Leu  Lys  Lys  Gly  Glu
               60                       65                       70

Asn  Lys  Phe  Gly  Tyr  Cys  Asn  Ser  Lys  Gly  Asn  Cys  Val  Glu  Arg  Asp
     75                            80                   85

Phe  Lys  Glu  Ser  Phe  Gly  Ile  Ser  Ile  Lys  Ile  Lys  Gly  Ile  Ser  Asn
90                            95                  100                      105

Lys  Gly  Asp  Asp  Glu  Pro  Ala  Cys  Pro  Gln  Tyr  Lys  Asn  Thr  Trp  Ile
                    110                 115                      120

Asn  Tyr  Gly  Lys  Cys  Asn  Glu  Pro  Tyr  Tyr  Cys  Gly  Thr  Asn  His  Gly
               125                 130                           135

Leu  Phe  Tyr  Ala  Asn  Lys  Arg  Lys  Leu  Asp  Tyr  Phe  Pro  Thr  Asp  Gly
          140                 145                      150

Glu  Lys  Cys  Asn  Ser  Asn  Asn  Ile  Pro  Tyr  Ala  Val  Cys  Tyr  Leu  Gly
     155                      160                 165

Arg  Cys  His  Thr  Thr  Gly  Gly  Phe  Phe  Ser  Glu  Phe  Gly  Thr  Ile  Val
170                      175                 180                           185

Lys  Asn  Val  Glu  Ile  Val  Thr  Leu  Ser  Asp  Gly  Lys  Asn  Ser  Ser  Arg
               190                 195                           200

Arg  Gly  Lys  His  Lys  Asn  Leu  Pro  Thr  Ser  Lys  Val  Phe  Asp  Ser  Tyr
               205                 210                      215

Ser  Ile  Tyr  Asp  Ile  Asp  Pro  Lys  Asn  Trp  Lys  Ile  Glu  Asp  Asp  Asp
          220                 225                      230

Lys  Asp  Val  Thr  Val  His  Glu  Asn  Thr  Leu  Asp  Pro  Lys  Ser  Asp  Ser
     235                 240                      245

Arg  Leu  Cys
250
```

(2) INFORMATION FOR SEQ ID NO:6:

(i) SEQUENCE CHARACTERISTICS:
        (A) LENGTH: 1241 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 119..985

(ix) FEATURE:
        (A) NAME/KEY: unsure
        (B) LOCATION: -103..-100

(ix) FEATURE:
        (A) NAME/KEY: unsure
        (B) LOCATION: 47..49

(xi) SEQUENCE DESCRIPTION: SEQ ID NO:6:

```
GAATTCCAAC  AACAGTGCCT  TTGGGCGGCC  GCACTGGTCT  TAACTTTTTT  CTCTTTTTTA        60

GCAGCGGCCA  TGATAATTTA  ATAATCTTAT  TTACAAATTT  TTTATTATTT  TATTCAGA         118

ATG  AAC  TTG  TAT  TTT  TTA  TTT  TTT  ATT  TCA  ACT  ATT  TTA  GCA  GCT  AAA   166
Met  Asn  Leu  Tyr  Phe  Leu  Phe  Phe  Ile  Ser  Thr  Ile  Leu  Ala  Ala  Lys
1              5                        10                       15

CCT  TTC  AAT  TCT  TTT  AAT  AAA  ACT  TCA  TTA  ATT  GAT  GAA  GGA  GTT  GAC   214
Pro  Phe  Asn  Ser  Phe  Asn  Lys  Thr  Ser  Leu  Ile  Asp  Glu  Gly  Val  Asp
                    20                       25                       30
```

| | | | | | | | | | | | | | | | | |
|---|---|---|---|---|---|---|---|---|---|---|---|---|---|---|---|---|
| AAC | GAT | GAC | GAT | ATT | GTC | TCT | AAA | AGA | GCA | GTA | GTT | ATT | GAT | TAT | TGT | 262 |
| Asn | Asp | Asp | Asp | Ile | Val | Ser | Lys | Arg | Ala | Val | Val | Ile | Asp | Tyr | Cys | |
| | | 35 | | | | | 40 | | | | | 45 | | | | |
| GAT | ACT | AGA | CAT | CCA | AAT | AAT | TTA | TGT | AAA | AAA | TAT | TTT | GAA | ATC | GAT | 310 |
| Asp | Thr | Arg | His | Pro | Asn | Asn | Leu | Cys | Lys | Lys | Tyr | Phe | Glu | Ile | Asp | |
| | 50 | | | | | 55 | | | | | 60 | | | | | |
| TCA | TAT | TGG | AAT | GAT | GAT | ACG | GAT | TGT | TTT | ACA | AAT | ATT | GGA | TGC | AAA | 358 |
| Ser | Tyr | Trp | Asn | Asp | Asp | Thr | Asp | Cys | Phe | Thr | Asn | Ile | Gly | Cys | Lys | |
| 65 | | | | | 70 | | | | | 75 | | | | | 80 | |
| GTA | TAT | GGA | GGA | TTT | GAT | ATT | ATT | GGT | GGT | AAA | GCT | CCT | AAA | ATT | GGA | 406 |
| Val | Tyr | Gly | Gly | Phe | Asp | Ile | Ile | Gly | Gly | Lys | Ala | Pro | Lys | Ile | Gly | |
| | | | | 85 | | | | | 90 | | | | | 95 | | |
| ACT | GTA | TGT | AGA | CTT | AAA | AAA | GGA | AAA | AAT | AAA | TTT | GGA | TAT | TGT | AAT | 454 |
| Thr | Val | Cys | Arg | Leu | Lys | Lys | Gly | Lys | Asn | Lys | Phe | Gly | Tyr | Cys | Asn | |
| | | | 100 | | | | | 105 | | | | | 110 | | | |
| TCA | AAA | GGA | AAT | TGC | GTT | GAA | AGA | GAT | TTT | ATT | GAA | AGT | TTT | GGA | GTA | 502 |
| Ser | Lys | Gly | Asn | Cys | Val | Glu | Arg | Asp | Phe | Ile | Glu | Ser | Phe | Gly | Val | |
| | | | 115 | | | | | 120 | | | | | 125 | | | |
| TCT | ATA | AAA | ATA | AAA | GGA | ATT | TCT | CAT | AGA | GGA | GAT | GAT | GAA | CCA | GCA | 550 |
| Ser | Ile | Lys | Ile | Lys | Gly | Ile | Ser | His | Arg | Gly | Asp | Asp | Glu | Pro | Ala | |
| | | 130 | | | | | 135 | | | | | 140 | | | | |
| TGT | CCA | CTT | TAT | GAA | AAT | ACT | TGG | ATT | AAT | TAT | GGA | AAA | TGT | AAT | GAA | 598 |
| Cys | Pro | Leu | Tyr | Glu | Asn | Thr | Trp | Ile | Asn | Tyr | Gly | Lys | Cys | Asn | Glu | |
| 145 | | | | | 150 | | | | | 155 | | | | | 160 | |
| CCT | TAT | CAT | TGT | GGA | ACA | AAT | TAT | GGG | TTA | TTT | TAT | GCA | AAC | AAA | AGA | 646 |
| Pro | Tyr | His | Cys | Gly | Thr | Asn | Tyr | Gly | Leu | Phe | Tyr | Ala | Asn | Lys | Arg | |
| | | | | 165 | | | | | 170 | | | | | 175 | | |
| AAA | CTC | AAT | TAC | TTT | CCT | GAT | AAC | GGT | CAA | AAA | TGT | AAT | TCA | AAA | TAT | 694 |
| Lys | Leu | Asn | Tyr | Phe | Pro | Asp | Asn | Gly | Gln | Lys | Cys | Asn | Ser | Lys | Tyr | |
| | | | | 180 | | | | | 185 | | | | | 190 | | |
| GAA | ATA | TAC | GGT | GTA | TGT | TAT | TTA | GGA | CGC | TGT | CAT | GGA | ACA | GGA | AAT | 742 |
| Glu | Ile | Tyr | Gly | Val | Cys | Tyr | Leu | Gly | Arg | Cys | His | Gly | Thr | Gly | Asn | |
| | | 195 | | | | | 200 | | | | | 205 | | | | |
| TTT | TCA | AAT | GGT | GAA | GTT | TTT | AGT | GAA | TTT | GGA | ACT | ATT | TTT | AAA | GAT | 790 |
| Phe | Ser | Asn | Gly | Glu | Val | Phe | Ser | Glu | Phe | Gly | Thr | Ile | Phe | Lys | Asp | |
| | 210 | | | | | 215 | | | | | 220 | | | | | |
| GTC | GAA | ATT | GTA | ACT | TTA | TCA | GAT | GGA | AAG | AAC | AGT | TCT | AAA | AGA | GGA | 838 |
| Val | Glu | Ile | Val | Thr | Leu | Ser | Asp | Gly | Lys | Asn | Ser | Ser | Lys | Arg | Gly | |
| 225 | | | | | 230 | | | | | 235 | | | | | 240 | |
| AAA | CAT | AAA | AAT | TTA | CAT | GGT | TCT | AAA | GTA | TTT | GAT | AGT | AAT | GGT | ATA | 886 |
| Lys | His | Lys | Asn | Leu | His | Gly | Ser | Lys | Val | Phe | Asp | Ser | Asn | Gly | Ile | |
| | | | | 245 | | | | | 250 | | | | | 255 | | |
| TAT | GAT | ATT | GAT | CCT | AAA | AAT | TGG | AAA | ATT | GAA | GAT | GAT | GAT | AAA | GAT | 934 |
| Tyr | Asp | Ile | Asp | Pro | Lys | Asn | Trp | Lys | Ile | Glu | Asp | Asp | Asp | Lys | Asp | |
| | | | 260 | | | | | 265 | | | | | 270 | | | |
| ATT | ACT | GTT | CAT | GAA | AAT | GCT | GGA | GAT | CCA | AAA | AGT | GAT | TCA | AGA | CGT | 982 |
| Ile | Thr | Val | His | Glu | Asn | Ala | Gly | Asp | Pro | Lys | Ser | Asp | Ser | Arg | Arg | |
| | | 275 | | | | | 280 | | | | | 285 | | | | |

TGT TAAATTTTA AATATTTGAT TTTTTTAAA TAAATATAAA TCTATATATT    1035
Cys

TAATAATATA ATTTCTTTTA ATTTTAAAT TAGTAAAATT TCGATAATTT TACTTAATTT    1095

TTTAAATTTA CTAAATTGAC TAATTTTATT AAGAAGTAAC TTCTAAAAAA TTTGATTTTT    1155

TTTAAAACAA ATAATTATAA ATATTTTTA ATTAAATAAA TTTAATAATT ACAAGATAAA    1215

AAAAAAAAAA AAAAAAAAG GAATTC    1241

( 2 ) INFORMATION FOR SEQ ID NO:7:

( i ) SEQUENCE CHARACTERISTICS:
        ( A ) LENGTH: 289 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Asn  Leu  Tyr  Phe  Leu  Phe  Phe  Ile  Ser  Thr  Ile  Leu  Ala  Ala  Lys
 1              5                        10                       15

Pro  Phe  Asn  Ser  Phe  Asn  Lys  Thr  Ser  Leu  Ile  Asp  Glu  Gly  Val  Asp
              20                       25                       30

Asn  Asp  Asp  Asp  Ile  Val  Ser  Lys  Arg  Ala  Val  Val  Ile  Asp  Tyr  Cys
         35                            40                       45

Asp  Thr  Arg  His  Pro  Asn  Asn  Leu  Cys  Lys  Lys  Tyr  Phe  Glu  Ile  Asp
     50                       55                       60

Ser  Tyr  Trp  Asn  Asp  Asp  Thr  Asp  Cys  Phe  Thr  Asn  Ile  Gly  Cys  Lys
 65                       70                       75                       80

Val  Tyr  Gly  Gly  Phe  Asp  Ile  Ile  Gly  Gly  Lys  Ala  Pro  Lys  Ile  Gly
                    85                       90                       95

Thr  Val  Cys  Arg  Leu  Lys  Lys  Gly  Lys  Asn  Lys  Phe  Gly  Tyr  Cys  Asn
               100                      105                      110

Ser  Lys  Gly  Asn  Cys  Val  Glu  Arg  Asp  Phe  Ile  Glu  Ser  Phe  Gly  Val
          115                      120                      125

Ser  Ile  Lys  Ile  Lys  Gly  Ile  Ser  His  Arg  Gly  Asp  Asp  Glu  Pro  Ala
     130                      135                      140

Cys  Pro  Leu  Tyr  Glu  Asn  Thr  Trp  Ile  Asn  Tyr  Gly  Lys  Cys  Asn  Glu
145                      150                      155                      160

Pro  Tyr  His  Cys  Gly  Thr  Asn  Tyr  Gly  Leu  Phe  Tyr  Ala  Asn  Lys  Arg
                    165                      170                      175

Lys  Leu  Asn  Tyr  Phe  Pro  Asp  Asn  Gly  Gln  Lys  Cys  Asn  Ser  Lys  Tyr
               180                      185                      190

Glu  Ile  Tyr  Gly  Val  Cys  Tyr  Leu  Gly  Arg  Cys  His  Gly  Thr  Gly  Asn
          195                      200                      205

Phe  Ser  Asn  Gly  Glu  Val  Phe  Ser  Glu  Phe  Gly  Thr  Ile  Phe  Lys  Asp
210                      215                      220

Val  Glu  Ile  Val  Thr  Leu  Ser  Asp  Gly  Lys  Asn  Ser  Ser  Lys  Arg  Gly
225                      230                      235                      240

Lys  His  Lys  Asn  Leu  His  Gly  Ser  Lys  Val  Phe  Asp  Ser  Asn  Gly  Ile
               245                      250                      255

Tyr  Asp  Ile  Asp  Pro  Lys  Asn  Trp  Lys  Ile  Glu  Asp  Asp  Lys  Asp
          260                      265                      270

Ile  Thr  Val  His  Glu  Asn  Ala  Gly  Asp  Pro  Lys  Ser  Asp  Ser  Arg  Arg
          275                      280                      285

Cys
```

( 2 ) INFORMATION FOR SEQ ID NO:8:

( i ) SEQUENCE CHARACTERISTICS:
        ( A ) LENGTH: 155 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:8:

```
TGTGTTAAAT TTTTAAAAAT TTGATTTTTT TTAAATAAAT GTCAATCTTT AAATTATTAA      60
TAAAATTTGG GAATTCCTGC AGCCCGGGGG ATCCACTAGT TCTAGAGCGG CCGCCACCGC     120
GTGGAGCTCA GCTTTGTTC CTTTAGTGAG GGTTA                                 155
```

( 2 ) INFORMATION FOR SEQ ID NO:9:

( i ) SEQUENCE CHARACTERISTICS:
    ( A ) LENGTH: 156 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:9:

| | | | | | | |
|---|---|---|---|---|---|---|
| TCCAAAAAGT | GATTCAAGAC | TGTGTTAAAT | TTTTAAAAAT | TTGATTTTTT | TTAAATAAAT | 60 |
| GTCAATCTTT | AAATTATTAA | TAAAATTTGT | AATTAAAGGA | ATTCCTGAAT | ATAAAAAATA | 120 |
| GTTTATTTGC | GAAATTAAAA | TTTTTTTTTT | CTATTT | | | 156 |

( 2 ) INFORMATION FOR SEQ ID NO:10:

( i ) SEQUENCE CHARACTERISTICS:
    ( A ) LENGTH: 76 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:10:

| | | | | | | |
|---|---|---|---|---|---|---|
| TTAAATAAAT | GTCAATCTTT | AAATTATTAA | TAAAATTGCA | TTTTAATATA | TCCTTGTAAA | 60 |
| CCCCAATTTT | CACCCC | | | | | 76 |

( 2 ) INFORMATION FOR SEQ ID NO:11:

( i ) SEQUENCE CHARACTERISTICS:
    ( A ) LENGTH: 163 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:11:

| | | | | | | |
|---|---|---|---|---|---|---|
| TCCAAAAAGT | GATTCAAGAC | TGTGTTAAAT | TTTTAAAAAT | TTGATTTTTT | TTAAATAAAT | 60 |
| GTCAATCTTT | AAATTATTAA | TAAAATTTGT | AATAGCCAGA | CAATATAATC | AAGATCTTTA | 120 |
| GACTTAAGAA | AGCTCTGCTT | TGCTGCTAGA | TGACTTGAAG | TCA | | 163 |

( 2 ) INFORMATION FOR SEQ ID NO:12:

( i ) SEQUENCE CHARACTERISTICS:
    ( A ) LENGTH: 211 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:12:

| | | | | | | |
|---|---|---|---|---|---|---|
| TTTTAAAAAT | TTGATTTTTT | TTAAATAAAT | GTCAATCTTT | AAATTATTAA | TAAAATTTGT | 60 |
| AACTCTATCC | ATTCTCTCCT | CAACTGTTTT | AACAGCAGCC | CGAGCCAAGC | CAAATCATCT | 120 |
| TTGATCTTTT | TTGAACGATC | TTATAGCAAA | ATGTTGAATA | CTGTTCTCAA | ACAAAATTTA | 180 |
| GATGAGTCTG | ATCCAGAATT | GTTTGATCTA | A | | | 211 |

( 2 ) INFORMATION FOR SEQ ID NO:13:

( i ) SEQUENCE CHARACTERISTICS:
    ( A ) LENGTH: 210 base pairs
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO:13:

| | | | | | |
|---|---|---|---|---|---|
| TTTTAAAAAT | TTGATTTTTT | TTAAATAAAT | GTCAATCTTT | AAATTATTAA | TAAAATAATT | 60
| TAATTGGGGT | AATTATTTGA | GATTACAAAT | AATTTTTTAT | TTTAGAACTA | TTTTTTTAGT | 120
| TTTGATAAA | ATACTTTAGG | GATAACAGCG | TAATTAATTT | ATTTAGATCT | TATATATAAA | 180
| TTAGATTGCG | ACCTCGATGT | TGGTTTGAAA | | | | 210

( 2 ) INFORMATION FOR SEQ ID NO:14:

( i ) SEQUENCE CHARACTERISTICS:
        ( A ) LENGTH: 319 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO:14:

| | | | | | |
|---|---|---|---|---|---|
| TCCAAAAAGT | GATTCAAGAC | GTTGTTAAAT | TTTAAATAT | TTGATTTTTT | TTAAATAAAT | 60
| ATAAATCTAT | ATATTTAATA | ATATAATTTC | TTTTAATTTT | TAAATTAGTA | AAATTTCGAT | 120
| AATTTTACTT | AATTTTTTAA | ATTTACTAAA | TTGACTAATT | TTATTAAGAA | GTAACTTCTA | 180
| AAAATTTGAT | TTTTTTTAAA | ACAAATAATT | ATAAATATTT | TTAATTAAA | TAAATTTAAT | 240
| AATTACAAGA | TAAAAAAAAA | AAAAAAAAAA | AAAGGAATTC | CTGCAGCCGG | GATCACTAGT | 300
| CTAGAGCGCG | CACCCTCAC | | | | | 319

( 2 ) INFORMATION FOR SEQ ID NO:15:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| CTRTTRCCGT | TRCACCTCAG | GCACGCGCGG | CACCACTAGC | TRATGAGGCT | RTAGGCGGTG | 60
| GG | | | | | | 62

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modifiedbase
        ( B ) LOCATION: 3
        ( D ) OTHER INFORMATION: /frequency=0.00
            / modbase=i
            / note="note"

( i x ) FEATURE:
        ( A ) NAME/KEY: modifiedbase
        ( B ) LOCATION: 6
        ( D ) OTHER INFORMATION: /modbase=i ( i x ) FEATURE:
        ( A ) NAME/KEY: modifiedbase
        ( B ) LOCATION: 12
        ( D ) OTHER INFORMATION: /modbase=i ( x i ) SEQUENCE DESCRIPTION: SEQ ID NO:16:

CTNTTNCCNT TNCANCT 17

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

GAATTCTAGA TCGATGGTAC C 21

( 2 ) INFORMATION FOR SEQ ID NO:18:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

```
GATATCTTGT TCGCCATCGT GGAATCAAAT AGATCAATGT CACTTTTCGA AAAATATACA      60
TGTTCAAATT TGATTTCAAT TTTATCGTGT TGGTAAACGT ACACTTTAAT TATTTTACTC     120
AAGTTGTGCG AAAGAGTCTT GTAAGGCAGT TTGATTTCTT TGCTTTCTCT CCACACCAAC     180
GGCACCAACG CGTTGGTATC TTTAGGCCAA TAAACAAATT TTTTGTGTTT GGAATTAGTC     240
TTTTTCACGC TTGATATTAT GTTATTGCAA GCGCTCTGAA TAGGTATACG AGTGCGAAAG     300
CCGTTTTCGT CGTACAAATC GAAATATTGT TGTGCCAGCG AATAATTAGG AACAATATAA     360
GAATTTAAAA CCAAGCTTGG CGCAAATAAA TAAGTATTTT ACTGTTTTCG TAACAGTTTT     420
GTAATAAAAA AACCTATAAA TAGATCTCGA GAATTCGAAT TCTAGATCGA TGGTACC       477
```

( 2 ) INFORMATION FOR SEQ ID NO:19:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

GAATTCTCGA GCTGCAGATC TGTCGACCCG GGAATAAAGA GCTCCAATC 49

( 2 ) INFORMATION FOR SEQ ID NO:20:

( i ) SEQUENCE CHARACTERISTICS:
        ( A ) LENGTH: 239 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

```
GATGGGCCAA GCTTGGCGTT ATTGAATAAG AATTTAAAAA TCAATCATTT GTATACTGTA      60
AATTACATAC TGTTTTATTT AACAATAGAT ATCATGGAGA TAATTAAAAT GCCAAGCTTG     120
GCGCAAATAA ATAAGTATTT TACTGTTTTC GTAACAGTTT TGTAATAAAA AAACCTATAA     180
```

```
ATAGATCATC  GAATTCTCGA  GCTGCAGATC  TGTCGACCCG  GGAATAAAGA  GCTCCAATC           239
```

INSECT-SPECIFIC PARALYTIC NEUROTOXIN GENES FOR USE IN BIOLOGICAL INSECT CONTROL: METHODS AND COMPOSITIONS

This invention was made in part with funding from the National Institutes of Health (grant no. NS 26109). The United States government may have certain rights in this invention.

TECHNICAL FIELD

The present invention relates to methods and compositions for improved biological control of insect pests. More particularly, the present invention relates to the use and manipulation of genes encoding insect-specific paralytic toxins for the development of improved biological insect control agents. The present invention specifically relates to baculoviruses genetically engineered to express an insect-specific paralytic neurotoxin gene derived from an insect-parasitic mite.

BACKGROUND OF THE INVENTION

*Pyemotes tritici,* the straw-itch mite, is one of thirteen known species of mites in the genus Pyemotes, all of which are predatory and which possess venoms causing mild to extreme toxicity in target insects. The thirteen known species can be divided into two morphological groups which also differ in host range, methods of dispersal and toxicity to their hosts, and in the effects of their toxins on insects and man. The scolyti and ventricosus groups are summarized in Table 1. Most members of the ventricosus group have extremely insect-toxic venoms. The scolyti mites are all phoretic, and are generally found on bark beetles; they may express paralytic toxins.

The mite life cycle takes only 7-14 days, with 100-300 newborn sexually mature mites emerging from the mother. When a female emerges, it immediately mates and finds a new host. The time for paralysis of a host insect is variable, and appears to depend on the species, size, developmental stage and number of attacking mites. All stages of host insects may be attacked by the mites, but adults are generally less susceptible due to their more sclerotized (i.e. harder) cuticles, which are more difficult for the mite mouthparts to penetrate.

The mite venoms themselves do not appear to be specific for particular insects, since the venoms are toxic to a wide variety of insect host and nonhost species. The toxin(s) cause irreversible paralysis without disrupting respiratory mechanisms (Weiser and Slama (1964) Ann. Ent. Soc. Am. 57:479).

Insect-specific toxins in the venom of *P. tritici,* have been purified and characterized (Tomalski et al. (1988) Toxicon 26:127-132; Tomalski et al. (1989) Toxicon 27:1151-1167). These toxins are produced in female mites and injected into insect prey as components of the venom, resulting in paralysis of the insect prey. The paralysis allows the feeding female mite to become fully gravid, thus ensuring adequate nutrients for reproduction. Low molecular weight toxin components cause rapid contractile muscle paralysis while a high molecular weight toxin fraction causes flaccid muscle paralysis.

One toxin component, designated TxP-I, has been purified to apparent homogeneity; it has an apparent molecular weight of 27,000, as determined by SDS-polyacrylamide gel electrophoresis. An analysis of the amino acid composition of TxP-I was presented in Tomalski et al. (1989), supra. The relatively high cysteine content could result in a number of disulfide bonds in the toxin molecule. The N-terminal sequence of TxP-I has been published: N-asp-asn-gly-asn-val-glu-ser-val-arg-ala-val-val-ile-asp-tyr-[Xaa]-asp-ile-arg-his-pro-(SEQ ID NO:1). The N-terminal amino acid sequence was not found to be homologous to any protein sequence in the Protein Identification Resource (National Biomedical Foundation Release No. 13, Jun. 30, 1987).

Two other components were resolved which exhibit molecular weights of 28,000 and 29,000; these two components comprise TxP-II. Based on peptide mapping and immunoblot experiments, it was postulated that the protein components of TxP-I and TxP-II are isoproteins (Tomalski et al. (1989) supra). The mixture of TxP-I and TxP-II comprise TxP-III.

Preparations of *P. tritici* toxins are not acutely toxic to mammals, as tested with mice by either intraperitoneal or intracerebral routes. The doses which cause paralysis of 50% of the test insects ($PD_{50}$) for TxP-I, TxP-II and TxP-III are 330, 550 and 500 micrograms/kg, respectively when tested with wax moth (*Galleria mellonella*) larvae. Txp-I and Txp-II cause rapid muscle-contracting paralysis.

Polyclonal antibody has been produced using purified TxP-I as the antigen. This antibody was reactive against both TxP-I and Txp-II, and the antibody neutralized the paralytic activity of partially purified preparations of TxP-III. (Tomalski et al. (1989) supra).

Insect-specific proteinaceous neurotoxins have been found in the venoms of other arthropods including scorpions, wasps and spiders (Zlotkin (1985) in *Comprehensive Insect Physiology, Biochemistry and Pharmacology.* I. *Insects.* I. Kerkut and L. I. Gilbert (eds.) Pergamon Press, Oxford, U.K., pp. 499-546. Several of the peptide toxins from scorpions exhibit insect-specific neurotoxic effects and have been sequenced. These scorpion toxins are of relatively low molecular weight, i.e. from about 3000 to about 8000 daltons, considerably different from the mite toxins. There is no apparent sequence relationship between the mite and scorpion toxins, but both mite and scorpion toxins have high cysteine content. Compact toxin protein structures are stabilized by disulfide bonds.

Interest in the biological control of insect pests has arisen as a result of disadvantages of conventional chemical pesticides. Chemical pesticides generally affect beneficial as well as nonbeneficial species. Insect pests tend to acquire resistance to such chemicals so that new insect pest populations can rapidly develop that are resistant to these pesticides. Furthermore, chemical residues pose environmental hazards and possible health concerns. Biological control presents an alternative means of pest control which can reduce dependence on chemical pesticides.

Strategies for biological control include the deployment of naturally-occurring organisms which are pathogenic to insects (entomopathogens) and the development of crops that are more resistant to insect pests. Approaches include the identification and characterization of insect genes or gene products which may serve as suitable targets for insect control agents, the identification and exploitation of previously unused microorganisms (including the modification of naturally-occurring nonpathogenic microorganisms to render them pathogenic to insects), the modification and refinement of currently used entomopathogens, and the development of genetically engineered crops which display greater resistance to insect pests.

Viruses that cause natural epizoptic diseases within specific insect populations are among the entomopathogens which have been developed as biological pesticides. Entomopathogenic viruses include the baculoviruses, entomopoxviruses, reoviridae (cytoplasmic polyhedrosis viruses), iridoviruses, parvoviruses, rhabdoviruses, picornaviruses, nodaviruses, ascoviruses (still unclassified) and probably certain retroviruses.

Baculoviruses are a large group of evolutionarily related viruses which infect only arthropods (Miller, L. K. (1981) in *Genetic Engineering in the Plant Sciences.* N. Panopoulous, (ed.), Praeger publ., New York, pp. 203–224; Carstens, (1980) Trends in Biochemical Science 52:107–110; Harrap and Payne (1979) in *Advances in Virus Research.* Vol. 25, Lawfer et al. (eds.), Academic Press, New York, pp. 273–355, Granados, R. R. and Federici, B. A. eds. (1986) *The Biology of Baculoviruses,* Volume 1, *Biological Properties and Molecular Biology* CRC Press Inc., Boca Raton, Florida). Some baculoviruses only infect insects which are pests of commercially important agricultural and forestry crops. Other baculoviruses are known which specifically infect other insect pests, e.g., mosquitoes and fleas. Such baculoviruses are potentially valuable as biological control agents. A potential advantage of baculoviruses as biological pesticides is their host specificity. Baculoviruses as a group infect only arthropods, and individual baculovirus strains usually only infect one or a few species of insects. Thus, they pose little or no risk to man or the environment, and can be used without adversely affecting beneficial insect species.

Baculovirus subgroups include nuclear polyhedrosis viruses (NPV), granulosis viruses (GV), and nonoccluded baculoviruses. In the occluded forms of baculoviruses, the virions (enveloped nucleocapsids) are embedded in a crystalline protein matrix. This structure, referred to as an inclusion or occlusion body, is the form found extraorganismally in nature and is responsible for spreading the infection between organisms. The characteristic feature of the NPV group is that many virions are embedded in each occlusion body, which is relatively large (up to 5 micrometers). Occlusion bodies of the GV group are smaller and contain a single virion each. The crystalline protein matrix of the occlusion bodies of both forms is primarily composed of a single 25,000 to 33,000 dalton polypeptide which is known as polyhedrin or granulin. Nonoccluded baculoviruses do not produce a polyhedrin protein, and do not form occlusion bodies. Gröner et al. in *The Biology of Baculoviruses,* Volume 1, p, which is incorporated by reference herein, in Chapter 9, Tables 2 and 7 provides an extensive list of NPV hosts and GV hosts, for example.

In nature, infection is initiated when an insect ingests food contaminated with baculovirus particles, typically in the form of occlusion bodies. The occlusion bodies dissociate under the alkaline conditions of the insect midgut, releasing the virions which then invade epithelial cells lining the gut. Within a host cell, the baculovirus migrates to the nucleus where replication takes place. Initially, specific viral proteins are produced within the infected cell via the transcription and translation of so-called "early genes." Among other functions, these proteins are required for the replication of the viral DNA, which begins 4 to 6 hours after the virus enters the cell. Viral DNA replication proceeds up to about 24 hours post-infection (pi). From about 8 to 24 hours pi, infected cells express "late genes" at high levels. These include components of the nucleocapsid which surround the viral DNA during the formation of progeny virus particles. Production of progeny virus particles begins around 12 hours pi. Initially, progeny virus migrate to the cell membrane where they acquire an envelope as they bud out from the surface of the cell. The nonoccluded virus particles can then infect other cells within the insect. Polyhedrin synthesis begins approximately 18 hours after infection and increases to very high levels by 24 to 48 hours pi. At about 24 hrs pi, there is a decrease in the rate of nonoccluded virus production, and most progeny virus particles are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects. (Reviewed in *The Biology of Baculoviruses,* Vol. I and II, Granados and Federici (eds.), CRC Press, Boca Raton, Florida, 1986.)

Baculoviruses which are derivatives of AcMNPV which are useful as expression vectors have been described in U.S. patent application Ser. No. 07/353,847, filed May 17, 1989 International Patent Application PCT/US90/02814, filed May 17, 1990; Rankin et al. (1988) Gene 70:39–49; Ooi et al. (1989) J. Mol. Biol. 210:721–736, Thiem and Miller (1990) Gene 91:87–95, all of which are incorporated by reference herein. Particularly strong late and very late promoters are described and include the modified polyhedrin promoter LSXIV, the hybrid Cap/Polh promoter and the synthetic promoter Syn.

Baculoviruses which exhibit improved insecticidal properties have been described. For example, AcMNPV in which the egt (ecdysone glucosyl transferase) gene has been inactivated causes earlier cessation of feeding and earlier larvae death as compared to larvae infected with wild-type AcMNPV (O'Reilly and Miller (1989) Science 245:1110–1112; O'Reilly and Miller (1990) J. Virol. 64:1321–1328; U.S. Pat. No. 5,180,580.

Egt− AcMNPV which have been further genetically altered to express a protein affecting ecdysis can provide additional improvements in insecticidal properties (International Patent Application PCT/US90/03758, filed Jun. 29, 1990, which is incorporated by reference herein). Egt− AcMNPV derivatives which express juvenile hormone esterase, eclosion hormone, or prothoracicotropic hormone have been constructed. Feeding times of infected larvae were reduced and death occurred earlier than in larvae infected with wild-type or Egt− AcMNPV.

Maeda (1989) Biochem. Biophys. Res. Commun. 165:1177–1183, has also described a genetically engineered baculovirus with improved pesticidal properties. BmNPV, which infects the silkworm *Bombyx mori,* has been modified to express a synthetic gene encoding the diuretic hormone of the tobacco hornworm *Manduca sexta.* The fluid balance of infected insects was disrupted, and killing was about 20% faster than with the wild-type virus.

Dee and co-Workers 1990) Bio/Technology 8:339–342, have cloned and expressed the insecticidal toxin from the scorpion *Androctonus australis* in mouse fibroblast cells. The coding sequence was fused to the signal peptide sequence of human interleukin-2 and synthesis was directed by promoter sequences in the long terminal repeat of Moloney murine sarcoma virus. The recombinant protein, which was secreted into the extracellular medium, was reported to be toxic to mosquito larvae but not to mouse cells in culture or to mice.

A gene encoding an insect toxin from *Buthus eupeus* (middle-Asian subspecies of scorpion) has been synthesized, cloned into the genome of AcMNPV (a nuclear polyhedrosis virus from *Autographa californica*) and expressed under polyhedrin promoter control. Constructions were also made in which the scorpion toxin was expressed from a synthetic gene comprising the toxin coding sequence fused to a signal-peptide coding sequence or as a fusion protein with 58 amino acids of polyhedrin at the N-terminus. In all cases there was some expression as determined by [$^{35}$S]-methionine radiolabeling SDS-polyacrylamide gel electrophoresis and autoradiography, but there was no insect-paralytic activity observed for any of the expression products. It was believed that this was in part due to protein instability, but the failure to detect biological activity may have been the result of insufficient sensitivity in the assay system or due to failure of the recombinant protein to form a functional three-dimensional structure (Carbonell et al. (1988) Gene 73:408–418).

Hammock et al. (1990) Nature 344:458–461 describes the baculovirus-mediated expression of an insect gene encoding juvenile hormone esterase (JHE), an enzyme which inactivates a developmental hormone.

Merryweather et al. (1990) J. Gen. Virology 71:1535–1544 reports the construction of baculovirus containing the *Bacillus thurinoiensis* subsp. *kurstaki* HD-73 delta endotoxin. The BTk HD-73 endotoxin gene is placed under the control of the polyhedrin promoter.

SUMMARY OF THE INVENTION

It is an object of the present invention to provide genes encoding insect paralytic neurotoxins, for example, from insect-parasitic mites such as those of the genus Pyemotes, particularly those from ventricosus group of the Pyemotes. In a specific embodiment the insect paralytic neurotoxin gene is the Tox34 gene of *Pyemotes tritici*, which is identified by the nucleotide sequence given in Table 2 (SEQ ID NO:4); a second specific embodiment of an insect paralytic neurotoxin and the gene which encodes it is provided in the nucleotide and amino acid sequences of Tox21a also of *Pyemotes tritici* in Table 4 (SEQ ID NO:6 and SEQ ID NO:7). It will be understood in the art that other insect-specific paralytic neurotoxin genes can be isolated and identified by nucleotide sequence homology, as determined in hybridization experiments (See, e.g., Hames and Higgins (1985) *Nucleic Acid Hybridization*. IRL Press, Washington, D.C.) employing sequence information provided herein.

Insect-specific paralytic neurotoxin genes having at least about 70% nucleic acid homology to the Tox34 (SEQ ID NO:4) or Tox21a (SEQ ID NO:6) coding sequences can be readily isolated employing well-known hybridization assays or screens. Such procedures are particularly useful for the isolation of such neurotoxin genes from insect-parasitic mites, and most particularly from mites of the genus Pyemotes. Functional equivalents of the insect-specific paralytic neurotoxins of the present invention, as exemplified by Tox34 and Tox21a, are proteins having the biological activity of Tox34 and/or Tox21a and which are substantially similar in structure, i.e., amino acid sequence, to Tox34 and/or Tox21a as given in Tables 2 and 4, respectively.

Neurotoxins substantially similar to Tox34 and Tox21a include those which are at least about 70% identical in amino acid sequence to Tox34 and/or Tox21a. Substantially similar neurotoxins also include those which have at least about 70% amino acid sequence similarity to Tox34 or Tox21a which allows conservative amino acid substitutions for the amino acids of Tox34 and Tox21a. It is appreciated by those in the art that protein function may be unaffected by minor structural modifications, particularly if those structural modifications are substitutions of amino acids which are similar in chemical and physical properties. Structural modification, including amino acid deletions and insertions, may be tolerated without effect on functionality.

Genes encoding neurotoxins which are functionally equivalent to Tox34 and/or Tox21a can be isolated and identified or otherwise prepared by any means known to the art especially by reliance on sequence information provided herein. For example, amino acid sequence homology and/or nucleotide sequence homology as measured by hybridization methods can be coupled with methods described herein for assessing insect neurotoxicity to isolate functional insect neurotoxins. PCR methods, for example, combined with other art-known techniques and the teachings herein can be employed to isolate genes encoding neurotoxins that are functionally equivalent to those of the present invention. The information provided herein coupled with known methodology regarding protein and DNA synthesis, conservation of properties between amino acids and codon usage allows those of ordinary skill in the art to readily design and synthesize insect neurotoxins and insect neurotoxin genes which are functional equivalents of Tox34 and Tox21a.

It is a further object of the invention to provide an insect control agent expressing an insect-specific paralytic neurotoxin gene, such as a baculovirus, e.g., AcMNPV, genetically engineered to express the neurotoxin gene, for example, a neurotoxin gene from an insect-parasitic mite. In such agents, the insect-specific neurotoxin gene is placed under the regulatory control of appropriate gene regulatory sequences, such as a promoter, such that an amount of the neurotoxin effective for producing a toxic effect, such as paralysis, in a targeted insect is produced. Specific embodiments of a genetically modified AcMNPV include vETL-Tox34, vCap/Polh-Tox34, vEV-Tox34, and vSp-Tox34, in which the Tox34 gene is expressed under the control of an early promoter, strong late, and/or a very late promoter; particularly preferred embodiments of a genetically modified, occluded AcMNPV is vSp-Tox34 which is an occluded virus, and vCap/Polh-Tox34, which is non-occluded but, exerts improved insect control earlier than other examples. The skilled artisan will understand how to construct an analogous occluded virus. The skilled artisan will also understand that a virus can be occluded by coinfection of cells with a helper virus which supplies polyhedrin gene function.

The skilled artisan will also understand how to construct recombinant viruses in which a toxin gene is inserted at other locations in the AcMNPV genome. Such viruses would have a toxin gene fused to an appropriate promoter inserted into any nonessential region of the AcMNPV genome. Nonessential regions include the p10 gene region (Adang and Miller, 1982, J. Virology 44:782–793; Kuzio et al., 1984. Virology 139:414–418), the DA26 gene region (O'Reilly et al., 1990, J. Gen. Virology, 71:1029–1037), the ETL region (Crawford and Miller, 1988, J. Virology, 62:2773–2781), the egt region (O'Reilly and Miller, 1990, J. Virology 64:1321–1328) the 603 open reading frame (orf) region (Gearing and Possee (1990) J. Gen. Virology 71:251–262), the p94 of region (Friesen and Miller (1987) J. Virology 61:2264–2272) or other regions which can readily be determined by the skilled artisan. Since there is significant homology among some genes of different baculoviruses, the skilled artisan will also understand how to insert the toxin gene, fused to an appropriate promoter, into the genomes of other baculoviruses in similar nonessential locations.

Another object of the invention is to provide an insect-toxic composition comprising an insect-toxic amount of an insect virus, such as a baculovirus, genetically engineered to express an insect-specific paralytic neurotoxin at a level that results in a toxic effect on a targeted insect, and an agriculturally or otherwise environmentally acceptable carrier. Such compositions can be employed for protection of plants from insect pests. Preferred control agents are those which express an insect-specific paralytic neurotoxin gene from an insect-parasitic mite, and particularly those mites of the genus Pyemotes. When the insect virus is a baculovirus of a GV or NPV group, it is preferred that the virus particles are present in the occluded form.

It is a further object of the invention to provide a method for the biological control of an insect pest comprising the step of applying an insect-toxic composition which contains an insect-toxic amount of an insect control agent genetically engineered to express an insect-specific paralytic neurotoxin gene from an insect-parasitic mite. Such an insect-toxic composition is applied in the vicinity of a targeted insect, an insect habitat or to an area, plant or environment that is to be protected from the insect pest. The amount of said control agent in said composition and the level of expression of said neurotoxin gene by said control agent are such that said composition produces a toxic effect in a targeted insect. Preferred insect control agents are insect viruses including the baculoviruses, particularly occluded viruses such as NPVs and GVs, more particularly AcMNPV and its derivatives and close relatives. The occluded forms of genetically altered nuclear polyhedrosis viruses will be most useful in the present invention. The skilled artisan understands that the genetically altered virus expressing the insect toxin may itself be capable of occlusion or that occlusion may be achieved by other means, e.g., by coinfection with an occlusion-positive virus.

Similarly, it is an object to provide insect control agents genetically altered to express an insect-specific paralytic neurotoxin gene, which agents are effective against insect pests other than those which attack or are harmful to plants. Such an agent can be incorporated into insect-toxic, insect-paralytic, or insecticidal compositions along with environmentally acceptable carriers as understood in the art, and can be used in a method to control a targeted insect pest susceptible to the particular insect control agent employed.

In addition to plant-protective insecticidal compositions, the insect control agents of the present invention can be used in the control of other insect pests with the choice of the particular organism genetically modified to express an insect-specific paralytic neurotoxin appropriate for the target insect pest. For example, there are baculoviruses known to specifically infect each of mosquitoes and fleas. See, Beard et al. (1989) J. Invertebrate Path. 54:128–131 and Federici (1980) Virology 100:1–9. As with insect pests which attack plants, the target insect guides the ordinary skilled artisan in the selection of the insect control agent employed to express paralytic toxin. The ordinary skilled artisan knows how to select an appropriate regulatory and/or promoter sequence appropriate for use with the insect control agent.

It is yet another object of the invention to provide a method for the production of an insect-specific paralytic neurotoxin in a cell in which it is not naturally expressed. Said method comprises the steps of constructing a recombinant DNA molecule in which the coding sequence of an insect-specific neurotoxin is under the control of regulatory sequence which effects expression of the coding sequence in a selected host cell, introducing the recombinant DNA molecule into the suitable host cell, and culturing said resulting recombinant host cell containing the recombinant DNA molecule under conditions which allow the expression of the insect toxin coding sequence. The neurotoxin coding sequence is, for example, inserted downstream of a promoter expressible in the host cell or infected host cell. The DNA molecule containing the expressible neurotoxin sequence can be introduced into the host cell employing vector sequences which facilitate its introduction. Culturing a host cell can include culturing of single cells in liquid media, cell tissue culture, or the propagation of cells engineered to express the neurotoxin gene in multicellular organisms, including higher organisms such as insects. In general, any method known in the art for introducing DNA into a host cell can be employed. The art knows, with the benefit of this disclosure, how to select host cells, plasmid or virus vector sequences, promoters, and neurotoxin genes suitable for such production. The insect-specific neurotoxins produced in such genetically altered host cell cultures, when appropriately delivered to a target insect, is toxic to that insect. Neurotoxins produced in such cultures may be employed.

BRIEF DESCRIPTION OF THE FIGURES

FIG. 2 compares the effects on weight gain in insect larvae infected by injection with either wild-type AcMNPV (L-1) or recombinant virus vEV-Tox34 as a function of time after infection. Mock infection controls (TC-100) were also included. Larvae were first observed 24 hr after injection (shown as 0 hrs post infection (pi)). Those which died as a result of the physical effects of injection were eliminated from the study at that time. The number of larvae in each group is shown (N). The larvae were weighed and their average weights, including the standard error are shown by the bars and extensions above each bar (scale on left gives average weight per larva in milligrams). The percentage of each larval group paralyzed with time is represented by a black central bar within the larger open bar representing average weight (scale on right side gives paralyzed or dead).

FIG. 7 compares the weight gains of pi T. ni larvae 12 hr first instar larvae after injection with $4 \times 10^5$ plaque-forming units of nonoccluded AcMNPV (L-1 ascending slash), vEV-Tox34 (open), vCap/Polh-Tox34 (shaded) vETL-Tox34 (cross-hatched) or vSp-Tox34 (stippled). Uninfected larvae (descending slash) were injected with 2 microliters of tissue culture fluid. Larvae were first weighed, then injected and placed on virus-free diet. Error bars denote $\pm 2 \times$ the standard error which contains 95% of the experimental measurements in a standard deviation. In lieu of other statistical analysis the means for which the error bars do not overlap can be considered significantly different at the 0.05 confidence level. In cases where the error bars were overlapping, a Student's t test for the pairwise comparison of two means (DECalc-PLUS Routine Library, Digital Equipment Corp., Merrimack, New Hampshire) or a Duncan's Multiple Range test (SAS Base/Stat Release 6.04, SAS Institute, Cary, North Carolina) was performed. Means which were not statistically different, were ranked and then given a letter (A, B, C . . .) to designate the highest to lowest mean weight for within day treatments above the S.E. bar.

DETAILED DESCRIPTION OF THE INVENTION

Figure 1:
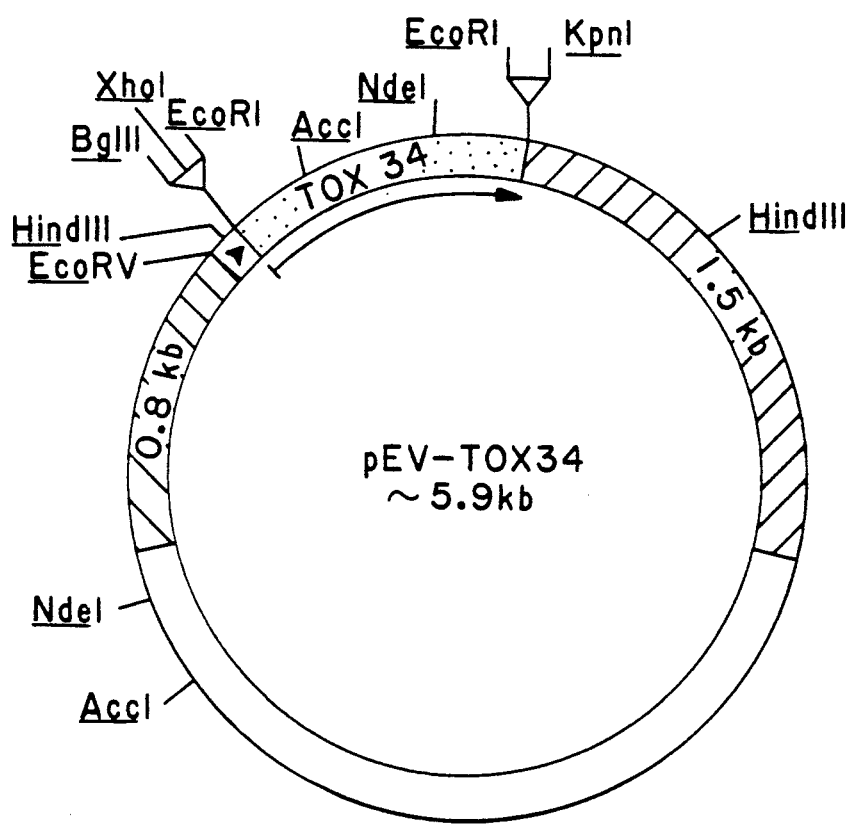
FIG. 1 illustrates the transplacement plasmid pEV-Tox34. This plasmid was used in the construction of the recombinant AcMNPV vEV-Tox34 by homologous recombination between wild-type virus and plasmid polyhedrin sequences. The 933 bp EcoRI fragment containing Tox34 was inserted into pEVmodXIV (described in U.S. patent application Ser. No. 353,847, filed May 17, 1989). The plasmid contains 2.6 kbp of vector sequences (open region), a 0.8 kbp region of the AcMNPV genome immediately upstream of the polyhedrin gene, a 1.5 kbp region of the AcMNPV genome from the KpnI site within the polyhedrin gene and extending downstream of the gene (AcMNPV sequences are shown as slashed lines), and the modified polyhedrin promoter LSXIV shown as a solid arrowhead between the EcoRV and BglII restriction sites. The direction of the Tox34 coding sequences (stippled line) from the LSXIV promoter is shown by an arrow inside the circle.

A biological insect control agent is an agent effective in the control of insect pests. Insect control agents which can be modified to express an insect-specific paralytic neurotoxin for use in the present invention include insect viruses, entomopathogenic bacteria and fungi, plant-colonizing bacteria, plants and plant viruses which are vectored by or may be incidentally ingested by insects. Control can refer to limitation of feeding behavior by or to killing of an insect pest. A biological insect control agent of the present invention must have an insect-toxic effect that is attributable at least in part to the expression of an insect-specific neurotoxin coding sequence. An insect-toxic effect relates to any adverse effect on a targeted insect and is observable as paralysis and/or killing of that insect or as a change in normal behavior of the targeted insect such as in feeding behavior, righting response or other stereotypic behaviors.

Insect-parasitic mites are those mites which feed on insects. Many of such mites inject venom into the insect hosts on which they feed. Such venom will contain insect-specific paralytic neurotoxins to immobilize the host insects. Mites which are most likely to express insect-specific paralytic toxin genes include those within the ventricosus group including *P. anobii, P. beckeri, P. emeroinatus, P. schwerdtfeoeri. P. tuberculatus. P. tritici. P. ventricosus and P. zwoelferi.*

An insect-specific paralytic neurotoxin is a polypeptide which causes paralysis of a sensitive insect. Larvae and/or adult insects may be affected by an insect paralytic neurotoxin. The paralytic effect of the neurotoxin may initially be observed as an effect on mobility or other behaviors of the insect including feeding behavior. Insect-specific neurotoxins are those which adversely affect insects, and have negligible effects on higher animals, especially mammals. The insect-specific paralytic neurotoxin of this invention is specifically exemplified by the gene products of Tox34 and Tox21a, and the TxP-I and TxP-II proteins produced by *P. tritici.* The deduced amino acid sequences of two representative insect-specific paralytic proteins are presented in Tables 2 and 4. It is understood that any protein with an amino acid sequence which is substantially identical (at least about 70% identical or at least about 70% similar) to the amino acid sequence from the aspartate encoded at about nucleotide 118 to the cysteine encoded at about nucleotide 873 or is substantially identical to the sequence in Table 4 which has a measurable toxic effect on insects is a functional equivalent of the Tox34 or Tox21a proteins. Preferably, the amino acid sequence of an insect-specific paralytic neurotoxin is at least about 83% identical (with gaps in one sequence treated as nonidentical, not similar amino acids as compared with the sequences of Tables 2 or 4), or at least about 88% similar. A toxin that is functionally equivalent to the neurotoxins of this invention effects a similar muscle contractile paralysis in insects as is caused by Tox34 and Tox21a. It is well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff at. (1978) in *Atlas of Protein Sequence and Structure,* Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Additional functional equivalents of insect-specific paralytic neurotoxin as defined herein include polypeptides with portions of amino acid sequences with substantial identity to Tox34 or Tox21a or polypeptides which themselves are a portion of a full length TxP-I protein or which have the amino acid sequence of a Tox34 or Tox21a protein into which an insertion has been made, and which retain the biological activity of an insect-specific paralytic neurotoxin which effects contractile muscle paralysis.

Insect-specific paralytic neurotoxin genes may be found in insect-predacious mites, including but not limited to those listed in Table 1, particularly those within the ventricosus group, or in other insect parasites or predators. Genes homologous to the Tox34 and Tox21a genes of the present invention may be identified in mites or other sources by nucleic acid hybridization to sequences disclosed in the present invention or by cross-reaction of toxin molecules with antibody specific for the toxins of the present invention or by any other means known to the art, including the use of PCR technology carried out using oligonucleotides corresponding to conserved or unambiguous regions of the toxin gene(s) exemplified herein. In principle, any insect-specific paralytic neurotoxin gene may be identified and that gene expressed in a baculovirus vector. Biological activity of the expressed protein can be readily determined and similarly, the efficacy of such a genetically modified vector can be assessed using the teachings of the present invention in combination with art-known techniques.

A recombinant DNA molecule is one which has been produced either by natural processes using known methods and directed by man to produce a desired result or artificially produced from parts derived from heterologous sources, which parts may be naturally occurring or chemically synthesized molecules, and wherein those parts have been joined by ligation or other means known to the art.

Genetically modified to contain and express an insect-specific paralytic neurotoxin gene means that nucleotide sequences encoding such a protein and directing its synthesis are introduced into a biological insect control agent or host cell which did not naturally contain that gene so that the modified agent or cell can produce that neurotoxin protein. Any means known to the art may be used to insert the expressible neurotoxin gene into a particular insect control agent or host cell.

Any art-known regulatory sequences, promoter and/or promoter-associated sequences which direct gene expression in the desired infected or uninfected host or infected or uninfected host cell may be used to control transcription and translation of a nucleotide sequence encoding an insect-specific paralytic neurotoxin.

It will be understood that the goals of a skilled artisan will determine the choice of particular regulatory sequences or promoters. For example, with insect virus, e.g., baculovirus, promoters, if high levels of expression are required, then an especially strong late or very late promoter, synthetic promoter or hybrid promoter may be appropriate. When, however, the goal is to produce a paralytic neurotoxin to limit the feeding of an insect larva to the shortest possible time or to extend the effective host range of the insect virus, then it will be desirable to place the paralytic neurotoxin gene under the regulatory control of a baculovirus or nonbaculovirus (e.g., insect) promoter expressed early in the infection process.

An NPV baculovirus isolated from *Autographa californica* (Lepidoptera: Noctuidae), specifically AcMNPV is the insect virus exemplified in the present disclosure. The terms AcMNPV and AcNPV have been employed for the same viruses. The term AcMNPV is believed to currently be the more accepted in the art. The infectivity of most NPVs is reported to be restricted to members of the genus or family of the original host. See Grner (1986) supra. AcMNPV baculoviruses are reported to replicate in several families of Lepidoptera, but their infectivity is reported to be limited to that order. Other entomopathogenic viruses useful in the present invention include, but are not limited to, other baculoviruses, iridoviruses, parvoviruses, nodamuraviruses, CPVs, entomopoxviruses, ascoviruses and retroviruses. The art understands how to insert an expressible gene into a viral genome at a site which does not interfere with viral replicative functions. Similarly, the skilled artisan can select a promoter with desired strength and temporal expression to drive the expression of an insect-specific paralytic neurotoxin gene in a desired virus vector. The target insect will dictate the virus selected, and the particular virus to be engineered will guide the skilled artisan in the selection of an appropriate promoter.

As used herein, an insect control agent is a composition or the active ingredient of a composition which has an adverse affect on insect pests. Feeding by insects is reduced or other behaviors are affected in response to the insect control agent as a result of the expressed paralytic neurotoxin, and death of the insect ensues. An insect control agent of this invention preferably is an insect virus genetically engineered to express a heterologous gene encoding an insect-specific paralytic neurotoxin, but it may be an entomopathogenic fungus or bacterium which has been genetically engineered to express a heterologous gene encoding an insect-specific paralytic neurotoxin. Preferably, the toxin is secreted into the hemolymph of an insect infected with the genetically engineered entomopathogen.

Insecticidal compositions suitable for applications to plants to control insect pests comprise an agriculturally suitable carrier and an insect control agent. Application of an insecticidal composition of this invention can protect plants from insect pests by reducing feeding by and killing of susceptible insects.

The skilled artisan knows how to choose an insect control agent, e.g., an insect virus, which is suitable for the control of a particular insect pest. The skilled artisan also knows how to direct the expression of an insect-specific paralytic neurotoxin in a particular insect control agent or host cell.

It will be understood by those skilled in the art that the insect pests can be exposed to the insect control agent of the present invention by conventional methods including ingestion, inhalation or direct contact of the insect control agent.

Insect parasites, including bacteria, viruses, fungi, mites, nematodes, protozoa and insects, can also be genetically modified to express an insect-specific paralytic neurotoxin gene. Parasitism or infection of appropriate insects by such insect parasites will result in paralysis of those insects in addition to symptomology normally associated with the unmodified parasite. The paralysis of infected insects exacerbates the insect disease state. Feeding by and infection of the insect pest will reduce feeding and hasten death. Specific examples of such toxin proteins include, but are not limited to, Tox34 and Tox21a.

DNA sequences encoding an insect-specific paralytic neurotoxin as disclosed herein, expressed under the regulatory control of a promoter appropriate to the organism, may be used to genetically modify an organism to produce an insect control agent. Target organisms for such genetic modification include insect parasites, plants and nonphytopathogenic plant-colonizing bacteria.

A primary use of the genetically engineered insect control agents, preferably baculoviruses, of the present invention will be as components of agricultural compositions for applying to plants, plant environments or distributed in baits to effect the biological control of insect pests. It will also be possible to use the insect control agents of the present invention in the control of other insect pests with the appropriate choice of the particular organism genetically modified to express an insect-specific paralytic neurotoxin. For example, there are baculoviruses known to specifically infect each of mosquitoes and fleas. The target insect guides the skilled artisan in the selection of the insect control agent expressing the paralytic toxin, and the particular agent constrains the selection of an appropriate promoter sequence. Many variations of preparing such agriculturally suitable and/or environmentally acceptable compositions for insect control are known in the art.

The concentration of the insect control agent that will be required to produce insecticidally effective compositions for the control of an insect pest will depend on the type of organism and neurotoxin used and the formulation of the composition. The insecticidally effective concentration of the insect control agent within the composition can readily be determined experimentally, as will be understood by the skilled artisan. For example, the insecticidally effective concentration of a virus can be readily determined using techniques known to the art.

Agricultural compositions for control of insect pests of plants must be suitable for agricultural use and dispersal in fields. Similarly, compositions for the control of other insect pests must be environmentally acceptable. Generally, components of the composition must be non-phytotoxic and not detrimental to the integrity of the occluded virus. Foliar applications must not damage or injure plant leaves. In addition to appropriate solid or, more preferably, liquid carriers, agricultural compositions may include sticking and adhesive agents, emulsifying and wetting agents, but no components which deter insect feeding or any viral functions. I t may also be desirable to add components which protect the insect control agent from UV inactivation or components which serve as adjuvants to increase the potency and/or virulence of an entomopathogen. Agricultural compositions for insect pest control may also include agents which stimulate insect feeding.

Reviews describing methods of application of biological insect control agents and methods and compositions agricultural application are available. See, for example, Couch and Ignoffo (1981) in *Microbial Control of Pests and Plant Disease* 1970–1980, Burges (ed.), chapter 34, pp. 621–634; Corke and Rishbeth, ibid, chapter 39, pp. 717–732; Brockwell (1980 in *Methods for Evaluating*

Nitrogen Fixation, Bergersen (ed.) pp. 417-388; Burton (1982) in Biological Nitrogen Fixation Technology for Tropical Agriculture. Graham and Harris (eds) pp. 105-114; and Roughley (1982) ibid, pp. 115-127; The Biology of Baculoviruses, Vol. II, supra, and references cited in the above.

This invention is illustrated by the following examples, which are not to be construed in any way as imposing limitations on the scope thereof. It is understood that resort can be made to various other embodiments, modifications, alternatives and equivalents of the procedures materials and techniques specifically described which, after reading the description herein, may suggest themselves to those skilled in the art without departing from the spirit of the present invention and/or the scope of the appended claims.

EXAMPLE 1

Cloning of the P. tritici TxP-I Gene

Total polyadenylated RNA was isolated from a combination of host-seeking and gravid (pregnant) female mites using protocols described in Davis et al. (1986) Basic Methods in Molecular Biology, Elsevier Science Publishing Co., New York; Jacobson (1987) Meth. Enzymol. 152:254. cDNAs were produced using this polyadenylated RNA as template. EcoRI linkers were added and the cDNAs were cloned into lambda ZAP-II (from Stratagene, La Jolla, California) to generate a cDNA library.

Six million plaques were screened using the polyclonal antibody raised against TxP-I described above according to the manufacturer's protocol (Stratagene, La Jolla, California). Numerous clones were significant cross-reaction to this antibody.

Starting with the most strongly immunopositive cDNA clones, eight different antibody-positive cDNA inserts were subcloned from lambda phage into plasmids and sequenced. Predicted open reading frames were used to search GENBANK (release 60.0) for protein sequence homologies. Four of those cDNA inserts, including the most strongly imunopositive cDNAs, encoded proteins which were significantly homologous with myosin, topoisomerase II, phosphoinositide-specific phospholipase C and heat shock protein 70. One clone contained multiple EcoRI fragments, and therefore was believed to contain multiple cDNA inserts. Attention was focused on one of the fragments of this recombinant plasmid because it showed weak hybridization to a partially degenerate 62 base probe. The hybridizing EcoRI fragment of this plasmid was downstream of three other EcoRI fragments and therefore, was relatively far removed in the original lambda clone from the phage promoter, which in the design of this vector system, drives gene expression for detection with antibodies. Therefore, it was surprising that the original lambda clone produced sufficient protein for the weak cross-reaction with the anti-TxP-I antibody that was observed, because it would have been expected that there would be little or no phage-driven expression from the distal insert. The hybridizing EcoRI fragment was sequenced; it contained an open reading frame predicted to encode a protein with an amino acid sequence identical to the 21 N-terminal amino acid sequence empirically determined for the mature TxP-I toxin.

The toxin-encoding fragment, designated Tox34, was cloned and sequenced using a sequencing kit and the manufacturer's protocol (Sequenase TM, U.S. Biochemical, Cleveland, Ohio). The nucleotide sequence for the first identified EcoRI fragment containing a TxP-I-homologous sequence (designated Tox34 ) is presented in Table 2 (SEQ ID NO:4) along with the deduced amino acid sequence. The amino acid sequence matching the N-terminal amino acid sequence of the mature toxin is underlined. The open reading frame extends upstream of the underlined sequence, suggesting that the toxin is synthesized as a pretoxin or a preprotoxin. The synthesis of the TxP-I in the form of a pretoxin or preprotoxin may facilitate secretion, toxin folding and/or toxin activation outside the cell. A comparison of the empirical amino acid composition and the deduced amino acid composition is presented in Table 3. The deduced amino acid sequence for TxP-I showed no significant homology with any other protein in GENBANK (release 60.0).

This EcoRI fragment was considered likely to encode TxP-I by the following criteria: being part of a lambda clone showing cross-reactivity with TxP-I specific antiserum, comprising a DNA sequence containing an open reading frame for a protein predicted to have a molecular weight of about 30 kDa and an open reading frame encoding a sequence identical with the 21 N-terminal amino acids (SEQ ID NO:1) of TxP-I, and an amino acid composition comparable to that of TxP-I. This fragment was designated Tox34 . The deduced amino acid sequence allows the assignment of the sixteenth amino acid of the mature toxin as cysteine.

EXAMPLE 2

Oligonucleotide Probes and Hybridization Experiments

Two oligonucleotide probes, the sequences of which were based on the N-terminal sequence of TxP-I as published in Tomalski et al. (1989) supra, were synthesized (see Table 7). Probe Pt-N1 (SEQ ID NO:16) was a mixture of 16 seventeen-mers using a partially degenerate nucleotide sequence deduced from the N-terminal six amino acids, and containing three inosine residues at degenerate codon positions. The probe was calculated to have a $T_d$ (the temperature at which half of the duplexes are dissociated) of 38 to 43° C. where $$T_d = 2^\circ\ C.\ (\text{number of } A+T \text{ residues}) + 4^\circ\ C.\ (\text{number of } G+C \text{ residues})$$

for duplexes 11–23 bases long in 1M $Na^+$. Plasmid DNA was rescued from immunopositive plaques using protocols supplied by Stratagene, La Jolla, California, cut with EcoRI (which excises the cDNA insert from the plasmid), fractionated by agarose gel electrophoresis and then blotted onto Zeta-probe TM cationized membrane (Bio-Rad Laboratories, Richmond California) by alkaline capillary transfer with 0.5M NaOH/1.5M NaCl. The filter was washed briefly in 2×SSC/0.1% SDS at room temperature (RT), prehybridized in hybridization buffer (6×SSC/5×Denhardt's solution/0.5% SDS/20 micrograms/ml calf thymus DNA/5% dextran sulfate) without probe for one hour, hybridized in fresh hybridization buffer containing ca. $1\times10^6$ cpm of radiolabeled oligonucleotide per ml for 14 hr at 28°–30° C. (about 10° C. less than the calculated estimate of the $T_d$ for Pt-N1). The blot was then washed twice in 2×SSC/0.1% SDS for 15 min each time at the hybridization temperature and then subjected to autoradiography at −80° C. in the presence of intensifying screens. After exposure, the blot was again washed in the same buffer at an increased temperature of 5° C. below the estimated $T_d$ and again autoradiographed. Washes were also repeated using temperatures at the $T_d$ minimum estimate (38° C.) and the estimated $T_d$ maximum (43° C.).

Insert fragments exhibiting hybridization under the most stringent conditions were sequenced as candidate TxP-I coding sequences. Certain nonhybridizing inserts were also sequenced because an incomplete TxP-I cDNA might lack the sequences homologous to the Pt-N1 probe (SEQ ID NO:16). There were cDNAs obtained which exhibited cross-reactivity to the TxP-I antiserum and were capable of hybridizing to the Pt-N1 probe (SEQ ID NO:16) but did not encode Txp-I.

A longer probe was designed because longer and minimally degenerate probes have greater specificity than shorter ones, and are therefore better suited to probe more complex sequences. Probe Pt-N2 was synthesized as a mixture of 32 sixty-two-mers; it represented the entire 21 amino acid N-terminal sequence (see Table 7 and SEQ ID NO:15). In the design of Pt-N2 (SEQ ID NO:15), degeneracies were introduced at the wobble position in some of the cases where there was a choice of two codons. It was believed that this limited degeneracy would provide for stretches of homology which would increase the specificity of the probe. A guess was made according to preferred codon usage in Drosophila, in cases where there were three or four choices at the wobble position. Hybridization conditions for probing either the lambda cDNA library or subcloned cDNA fragments as plasmid DNA with Pt-N2 (SEQ ID NO:15) were as described above, except that higher temperatures appropriate for the longer probe length were used: 40°–42° C. for low stringency hybridization and initial washing with subsequent washes at higher temperatures (52° C. and 68° C.) to increase stringency of hybridization.

The use of either probe for screening lambda plaque lifts was not successful; low stringency hybridizations gave blots with high backgrounds, while stringent conditions gave false positives. Neither probe successfully identified the Tox34 -containing lambda phage either in its purified form or from the cDNA library. Probe Pt-N1 (SEQ ID NO:15) hybridized to Bluescript ™ vector sequences, to several clones at low stringency, and to the hsp70-homologous sequence as well as to the Tox34 sequence. Pt-N2 hybridized to the Tox34 sequence (SEQ ID NO:4) at relatively low stringency as well as to the Bluescript ™ vector sequence. Tox34 (SEQ ID NO:4) was sequenced despite the absence of a convincing hybridization result. As noted above, Tox34 (SEQ ID NO:4) encodes a Txp-I protein.

EXAMPLE 3

Cloning of Other TxP-I-related Genes

The cDNA library was analyzed to determine whether it contained other sequences related to the Tox34 sequence (SEQ ID NO:4). The EcoRI fragment carrying the entire Tox34 gene (SEQ ID NO:4) was gel purified, radiolabeled to high specific activity (Feinberg et al. (1983) Anal. Biochem. 132:6–13; Addendum (1984) Anal. Biochem. 137:266–267) and used as a hybridization probe to isolate additional TxP-I-homologous sequences from the lambda ZAP-II cDNA library. Hybridization conditions were identical to those used above except that the hybridization was performed at 65°–68° C.

About 40 additional cDNA clones were isolated which exhibited significant homology to the TxP-I probe. These cDNA inserts were analyzed by restriction endonuclease digestion with EcoRI and Southern hybridization. The majority of the cDNA inserts were similar in size to the Tox34 EcoRI fragment (SEQ ID NO:4) used as the probe. None had the same 1.5 kbp of "upstream" fragments as found in the initial lambda isolate containing the Tox34 sequence (SEQ ID NO:4), adding weight to the conclusion that those "upstream" EcoRI fragments were due to artifactual cloning. It was noted, however, that several of the newly isolated EcoRI fragments containing cDNA inserts, which hybridized to the EcoRI fragment containing the Tox34 cDNA (SEQ ID NO:4), differed in size from the Tox34 EcoRI fragment (SEQ ID NO:4). Smaller cDNAs could theoretically be explained by incomplete cDNA synthesis, but larger ones were less readily accounted for.

To characterize the cDNA inserts which were larger than the initial TxP-I isolate, the 5' and 3' ends of the cDNAs were sequenced as described above using oligonucleotide matching sequence near the ends of the Tox34 cDNA insert (SEQ ID NO:4) as primers. The 5' ends of four larger cDNA inserts were sequenced using a primer located within the 5' end of the Tox34 open reading frame. The 5' end of one cDNA clone was essentially identical in size and nucleotide sequence to the Tox34 cDNA clone (SEQ ID NO:4). (it was lacking one nucleotide at the cloning site, which is a trivial difference). The 5' ends of the other three cDNA clones differed in length and sequence from the Tox34 cDNA clone (SEQ ID NO:4) Of these 3 clones, 2 encoded the identical N-terminal 13 amino acids as Tox34 but differed in the length and sequence of the upstream untranslated leader region. The third of these clones (the Tox21a clone; SEQ ID NO:6; SEQ ID NO:7) differed both in the N-terminal sequence (discussed below) and the upstream 5' translated leader region.

The 3' ends of seven toxin-related cDNAs were sequenced using a primer located within the 3' end of the Tox34 open reading frame (SEQ ID NO:4). The 3' ends of all the clones differed not only in size but in sequence as well. Approximately 60 bp downstream of the termination codon of the TxP-I open reading frame, the sequences of the inserts diverged substantially. This was not due to polyadenylation or to differences in vector sequences. Instead, it appears that the TxP-I-related genes are different due to genetic heterogeneity in the mites from which RNA was extracted for the cDNA library construction, or due to the existence of a multigene family of toxins within the mite genome. Table 5 compares the 3' ends of several toxin-related cDNA clones that were identified by probing the mite cDNA library with the Tox34 fragment. The sequences are aligned relative to the sequence of Tox34. Approximately 50 bases downstream of the end of the toxin coding region (+873 in Tox34), the sequences diverge. See SEQ ID NO:8 through SEQ ID NO:14.

A second cDNA insert (Tox21a) (SEQ ID NO:6) was sequenced in its entirety to study the nature of toxin gene diversity further. Oligonucleotide primers homologous to Tox34 (SEQ ID NO:4) were synthesized to aid the sequencing process. Because of the nucleotide diversity between the two genes, primers specific for some of the internal regions of the Tox21a insert (SEQ ID NO:6) were synthesized to allow completion of the sequence. Table 4 presents this sequence data. There were numerous differences in nucleotide sequence of Tox21a as compared with the Tox34 coding sequence, demonstrating that there is a diversity of toxin genes in the cDNA library, each encoding a TxP-I-related toxin, but differing somewhat in amino acid sequence. Table 6 presents a comparison of the deduced amino acide sequences for Tox34 and Tox21a (See also SEQ ID NO:5 and SEQ ID NO:7). The sequences are 88.9% similar and 82.8% identical. Two sequences of five amino acids each appear to be "inserted" in the Tox21a sequence (SEQ ID NO:7) when compared with the Tox34 sequence (SEQ ID NO:5). As a result, the predicted N-terminal sequence of the mature Tox21a gene product would not be the same as the N-terminal sequence determined empirically for TxP-I. Also, the first in-frame ATG of the Tox21a sequence (SEQ ID NO:6) aligns with the second in-frame ATG of the Tox34 sequence (SEQ ID NO:4). Thus, there may effectively be a deletion of 13 amino acids at the N-terminus of the putative preprotoxin form of Tox21a. The deletion would be predicted to have no effect on the amino acid sequence of the mature toxin while the first insertion would be at the very N-terminus of the toxin. All of the cysteine residues are conserved between the "mature" proteins consistent with these amino acids playing a role in the folding and three dimensional structure of the mature toxin.

EXAMPLE 4

Baculovirus Expression of the Tox34 Coding Sequence

To demonstrate that the cloned Tox34 gene (SEQ ID NO:4) does indeed encode an insect toxin, the Tox34 sequence was inserted into a baculovirus genome (AcMNPV) under the control of the strong very late promoter LSXIV, as described in International Patent Application PCT/US90/02814, filed May 17, 1990; Ooi et al. (1989) J. Molec Biol. 210:721-736; Rankin et al. (1988) Gene 70:39-49, all of which are incorporated by reference herein.

All viruses are originally derived from AcMNPV L-1 (Lee and Miller (1978) J. Virol. 27:754), and are plaque-purified and propagated in *Spodoptera frugiperda* IPLB-SF-21 cells (Sf cells) (Vaughn et al. (1977) *In Vitro* 13:213-217) in TC-100 medium (GIBCO, Grand Island, New York) as described previously (Lee and Miller (1978) supra; Miller et al. (1986) in *Genetic Engineering, Principles and Methods,* Vol. 8 (eds. J. Setlow and A. Hollaender), Plenum Press, New York, pp.277-298).

The first step was the construction of transplacement plasmid pEV-pTox34 (illustrated in FIG. 1). This transplacement plasmid allows the allelic replacement of the polyhedrin gene of AcMNPV with the Tox34 gene (SEQ ID NO:4) under the regulatory control of the strong LSXIV promoter.

pEV-Tox34 was constructed by inserting the EcoRI fragment containing the Tox34 coding sequence (SEQ ID NO:4) into EcoRI-cut pEVmodXIV, which supplied the powerful LSXIV promoter and sequences flanking the polyhedrin gene of AcMNPV. DNA of wild-type AcMNPV and pEV-Tox34 were cotransfected into insect cells as described in Miller et al. (1986) supra, and a recombinant virus was isolated and designated vEV-Tox34 after selection on the basis of its occlusion-negative phenotype and screening for the proper allelic replacement events by restriction endonuclease analysis and Southern hybridization.

Expression of the Tox34 gene (SEQ ID NO:4) in vEV-Tox34 -infected insect cells was tested as follows.

Sf cells were separately infected with AcMNPV and vEV-Tox34 as described in Lee et al. (1978) supra; Miller et al. (1986) supra, and the cell culture fluids from control (uninfected), AcMNPV and vEV-Tox34 -infected cells were collected after 48 hrs of infection. Larvae of the wax moth *Galleria mellonella* were each injected with 5 microliter aliquots of culture fluids. Insect larvae injected with the culture fluid from vEV-Tox34 -infected cells were paralyzed within 2 minutes whereas the insect larvae injected with fluid from wild-type AcMNPV-infected cells showed no paralytic response over an extended time period (several days). Paralyzed larvae were visually immobile, they lacked the righting response (the ability to turn themselves upright after turned onto their dorsal sides) and they failed to spin silk to line their burrows (a stereotypic behavior of wax moth larvae). Control larvae exhibited movement, the righting response and silk-spinning behavior. These results indicated that a neuroparalytic toxin was produced in the vEV-Tox34 -infected cells, but not in cells infected with wild-type AcMNPV, via expression of the Tox34 cDNA coding sequence (SEQ ID NO:4) and that this toxin was secreted into the extracellular medium. The type of paralysis exhibited by the Tox34 gene product resembled the paralysis observed when TxP-I, TxP-II and/or TxP-III is injected in larvae.

To test the ability of a baculovirus carrying the Tox34 gene to control insect larval feeding behavior during infection, insects were infected with vEV-Tox34 by injecting purified budded virus into the hemolymph of test larvae. *Trichoplusia ni* larvae in about early fourth instar were injected with TC-100 medium (mock-infected) or medium containing budded virus particles from cell cultures infected with either wild-type AcMNPV or vEV-Tox34 ($4 \times 10^5$ plaque-forming units of virus per larva). Control larvae included those larvae injected with culture medium or with wild-type AcMNPV. Insects injected with vEV-Tox34 were paralyzed (immobilized and lacked righting response) by 36 hr after injection.

EXAMPLE 5

Similarity of the Tox34 -encoded Proteins and TxP-I and TxP-II

Figure 8A:
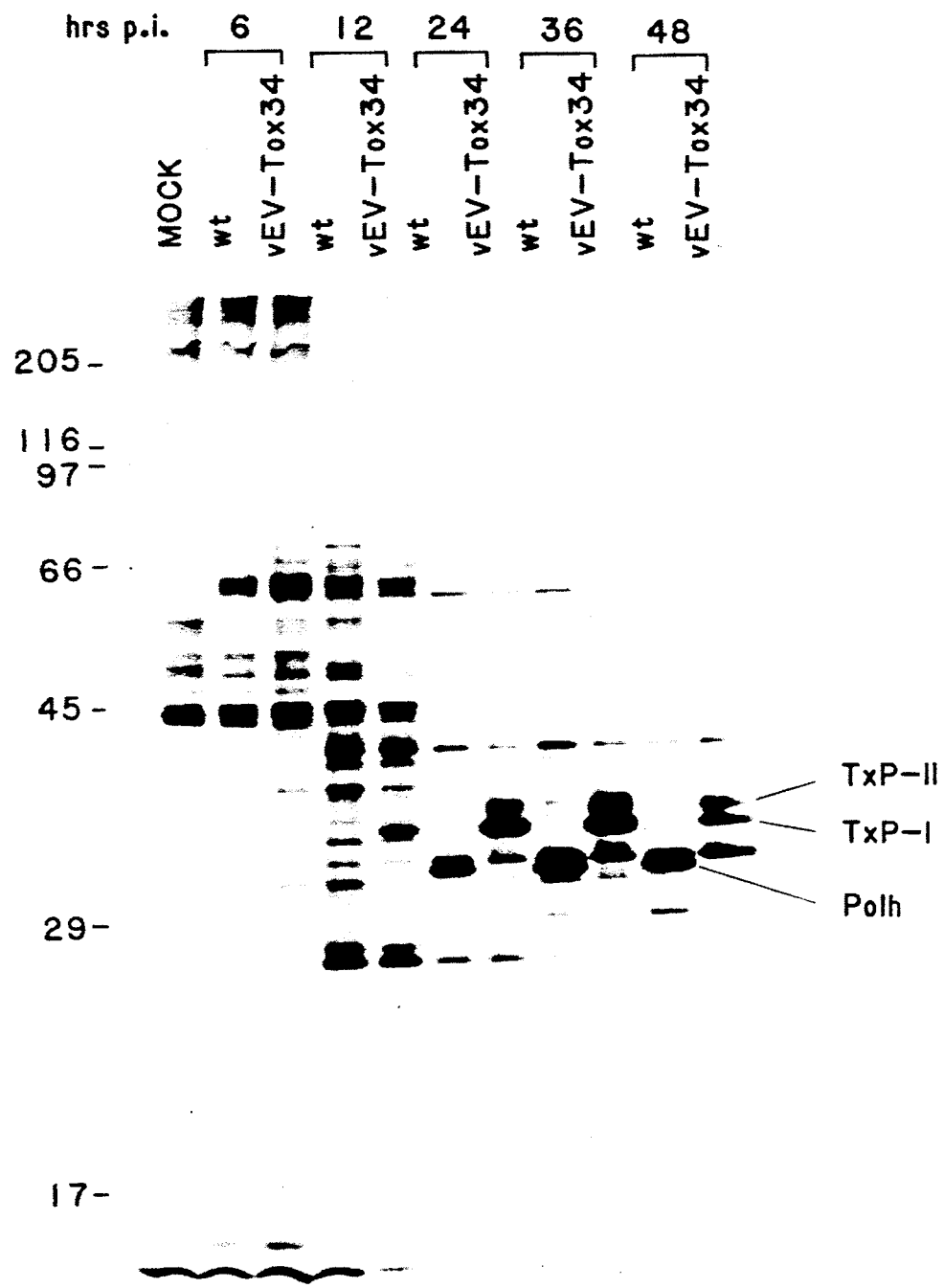
FIGS. 8A and 8B present autoradiograms of SDS-polyacrylamide gels that show the proteins produced from wt-AcMNPV or vEV-Tox34-infected S. frugiperda cells as a function of time after infection. After a 1 hr adsorption, the infected cells were pulse-labeled with [$^{35}$S]-cysteine at 6, 12, 24, 36 and 48 hrs pi. Proteins from tissue culture fluid (extracellular, Panel A) and from cell lysates (intracellular, Panel B) were denatured, reduced and electrophoresed 12% using polyacrylamide gels. The gels were impregnated with fluors, dried and used to expose X-ray film. Protein size standards were run in the far left lane of each gel and the molecular masses are noted. Proteins from uninfected cells are separated in the lane labeled mock (mock infection). The sources of the remaining proteins are indicated in each panel of the figure. The TxP-I, TxP-II and polyhedrin protein bands are indicated by arrows.
Figure 8B:
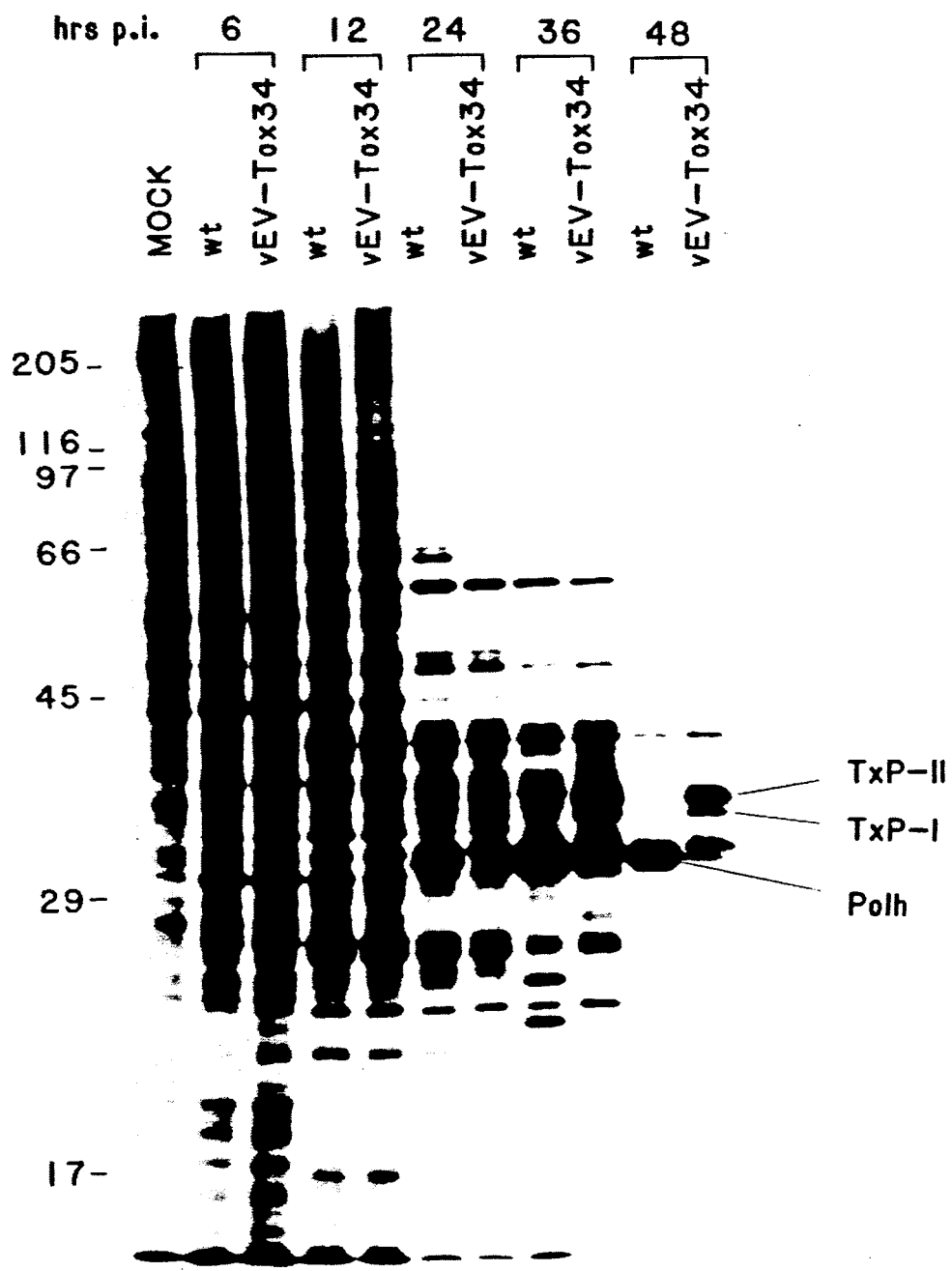

The sizes of the Tox34 gene products produced by vEV-Tox34-infected of Sr cells were examined by autoradiography after pulse labelling and SDS-polyacrylamide gel electrophoresis. After a 1 hr infection or mock infection period, cells were then labeled with [$^{35}$S]-cysteine at 6, 12, 24, 36 and 48 hrs post infection. Then labeling solution was removed and the cells were overlayered with unsupplemented TC-100 insect media and incubated an additional 2 hrs. Cells (containing intracellular proteins) and cell-free medium (containing secreted proteins) were collected separately. Cells were lysed. Intracellular and secreted proteins were denatured and reduced in buffer containing SDS and dithiothreitol, and then separated by SDS-polyacrylamide gel electrophoresis using 12% polyacrylamide gels. The gels were impregnated with fluors, dried and autoradiographed. The results are displayed in FIG. 8. Protein standards were run in the far left lanes and their molecular masses are given in kDa. Proteins from uninfected cells are separated in the lanes labeled "mock". Furthermore, the same change in mobility detected by SDS-PAGE is observed for the products of the Tox34 gene with reduction as observed for the proteins purified from the natural source. The presence of the three bands suggests that TxP-I (ca.27 kDa) and TxP-II (ca.28 kDa and ca.29 kDa) are related as mature toxin and protoxin and preprotoxin molecules. TxP-I, TxP-II and the polyhedrin protein bands are indicated in the figure by arrows. Txp-III comprises the three bands within TxP-I and TxP-II. FIG. 8 shows that the three proteins produced by vEV-Tox34-infected cells, correspond in size to the three toxin-related proteins described by Tomalski et al. (1988) sura: Tomalski et al. (1989) supra. Thus, the expression of the Tox34 coding sequence results in the production of TxP-I and TxP-II, which collectively constitute TxP-III. It is also possible, because Tox34 (SEQ ID NO:6) has two methionine codons near the 5' end of the coding region, one of which is not found in the Tox21a coding sequence (SEQ ID NO:6), that the two TxP-II protein bands may reflect alternate translational start sites. These possibilities can be distinguished by N-terminal sequencing each of the TxP-II component proteins or by site-directed mutagenesis of either one or both of the appropriate ATG codons.

EXAMPLE 6

Figure 2:
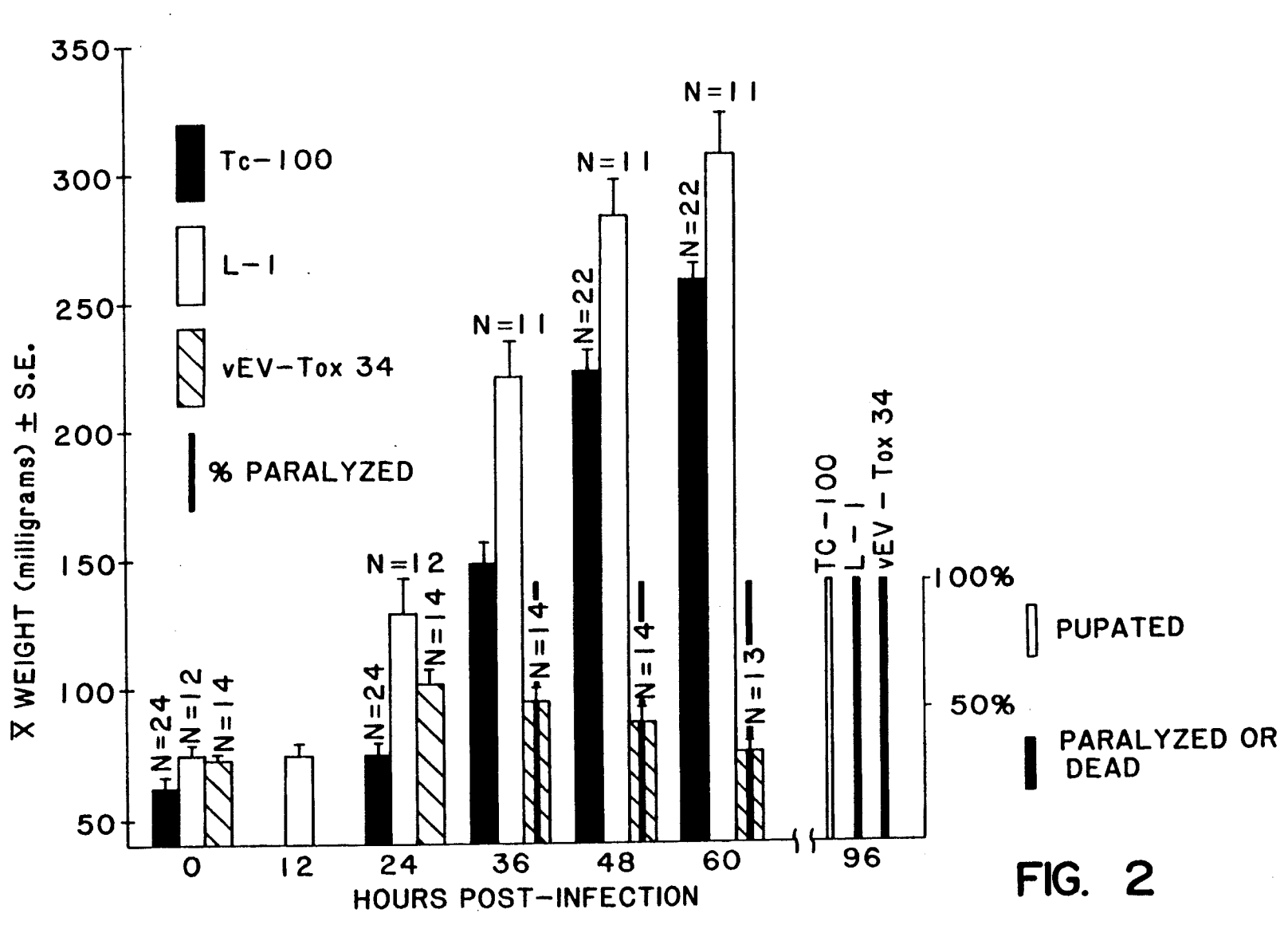

Additional AcMNPV Derivatives Genetically Engineered to Express a Mite Neurotoxin Gene To assess whether the expression of the TxP-I coding sequence improved AcMNPV as a pesticide, paralysis and weight gain by mock-infected insects (TC-100) and insects infected with wild-type AcMNPV (L-1) or vEV-Tox34 were compared. The results are illustrated in FIG. 2. At 24 after injection (a time taken as 0 hr post infection (pi) in this study) insect larvae from each group of control or test larvae weighed an average of 60–80 milligrams. By 24 hrs pi, insect larvae infected with wild-type AcMNPV had gained significantly more weight than mock-infected or vEV-Tox34 -infected larvae. It had been previously observed that wild-type virus infection actually increases larval feeding during the first days of infection (U.S. Pat. No. 5,180,580. By 36 hrs pi all the insects in the vEV-Tox34-infected group were paralyzed (immobile, no righting response) and none of the mock-infected or wild-type AcMNPV-infected larvae were paralyzed. The weight of the vEV-Tox34-infected larvae were significantly lower than insects in the two control groups; the weights of the vEV-Tox34-infected larvae actually declined in the period from 24 to 36 hrs pi. This may have been the result of water loss resulting from the failure to feed. This trend continued through 60 hrs pi. At 96 hr pi, all of the mock-infected larvae had pupated while the wild-type AcMNPV-infected and vEV-Tox34-infected larvae were dead or paralyzed. All virus-infected insects had typical signs of virus infection by this time. Thus, the expression of the mite toxin gene improved the properties of the baculovirus AcMNPV as a pesticide by inhibiting feeding during infection. The expression of the toxin does not block viral replication because all members of the vEV-Tox34-infected larval group died of a typical virus infection.

In the above-described virus construction, the Tox34 coding sequence is expressed under the regulatory control of the very late baculovirus promoter which is not expressed until about 18 hrs pi in cells infected at a high multiplicity of infection (moi; i.e. 10 viruses/cell) or until 24–30 hrs pi in cells infected at an moi of 1. Thus it was not unexpected that the paralytic effects of baculovirus-mediated Tox34 (SEQ ID NO:4) expression were not observed until about 36 hrs pi.

To attempt to accelerate the time at which the paralytic effects of the Tox34 gene product (See SEQ ID NO:5) could be observed, AcMNPV was genetically engineered to express the Tox34 coding sequence (See SEQ ID NO:4) under the control of other AcMNPV promoters.

Figure 3:
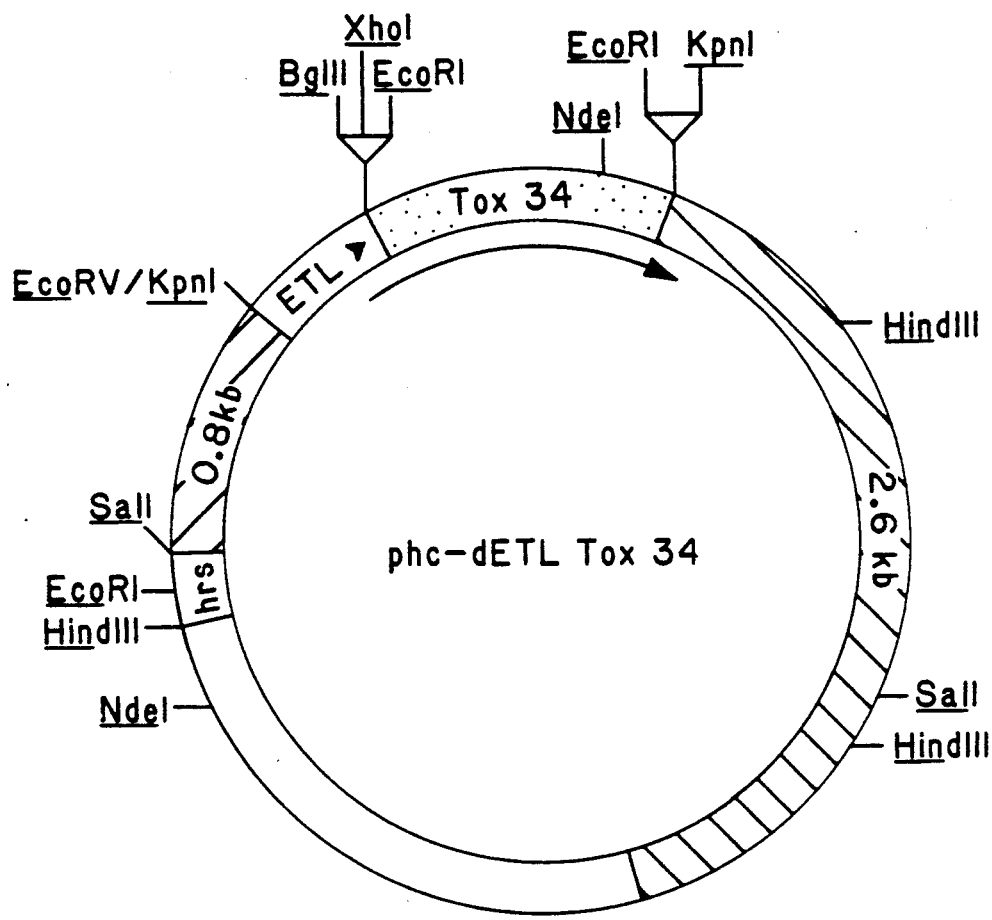
FIG. 3 illustrates transplacement plasmid phc-dETL-pTox34, which was used to construct the recombinant virus vETL-Tox34, which virus expresses TxP-I under the regulatory control of the early ETL promoter of AcMNPV. The BglII/KpnI fragment from pEV-Tox34 containing the Tox34 coding sequence (stippled line) was inserted into the BglII and KpnI sites of plasmid phc-dET, which was derived from phcwt (Rankin et al. (1988) supra) by replacing the polyhedrin promoter between the EcoRV and BglII sites with ETL promoter sequences (Crawford and Miller (1988) J. Virology 62:2773-2781) extending from $-300$ to $-6$ (relative to the translation initiation ATG codon designated $+1$, $+2$, $+3$). The ETL promoter is marked by a solid arrowhead. AcMNPV genomic sequences which drive homologous recombination and allelic replacement are shown by slashed lines; these sequences flank the ETL promoter/Tox34 fusion. An hr5 sequence of AcMNPV was originally inserted into phcwt for unrelated purposes; it is located on a HindIII-SalI fragment at the AcMNPV/vector junction shown at the left side of the diagram. Vector sequences are shown by an open line. Relevant restriction endonuclease sites are shown.
Figure 7:
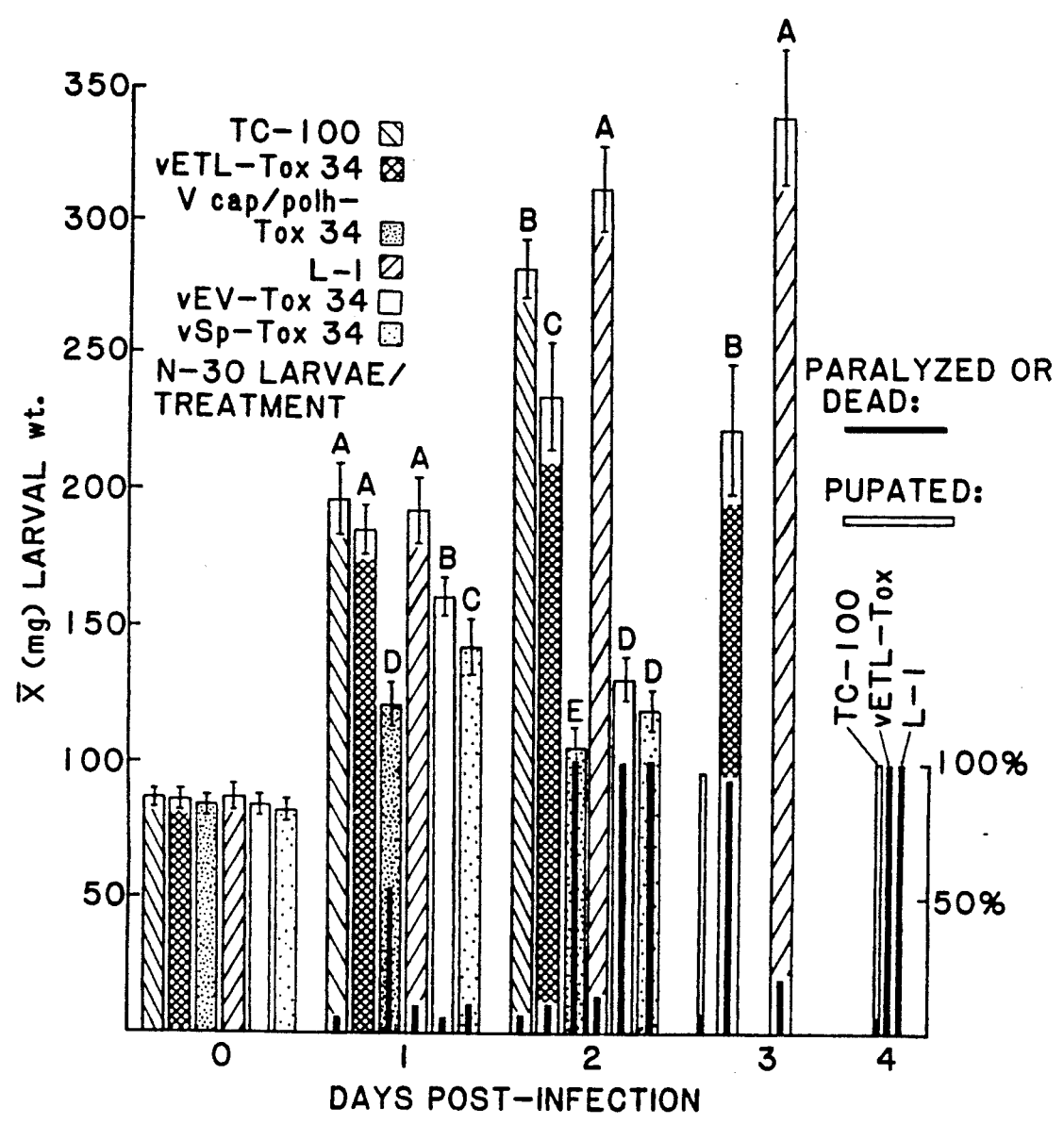

Transplacement plasmid phc-ETL-Tox34 (see FIG. 3) was constructed with the Tox34 coding sequence expressed under the regulatory control of the ETL promoter of AcMNPV (described in Crawford et al. (1988) J. Virol. 62:2773–2778 which is incorporated by reference herein). The Tox34-containing EcoRI fragment (See SEQ ID NO:4) was inserted into the EcoRI site of phc-dET, which was derived from phcwt (Rankin et al. (1988) supra) by replacing the polyhedrin promoter between the EcoRV site and the BlII site with the ETL promoter sequences extending from −6 (relative to the ETL translational initiation ATG at +1,+2,+3) to approximately 300 bp upstream of the ETL coding sequences. The transplacement plasmid and wild-type AcMNPV were cotransfected and appropriate nonoccluded recombinants were isolated and characterized. FIG. 7 presents data for insect infections with vETL-Tox34.

The Cap/Polh promoter (See SEQ ID NO:17) has been described by Thiem and Miller (1990) Gene 91:87–95, which is incorporated by reference herein; it is the same promoter as that designated vp39/LSXIV in FIG. 19 of U.S patent application Ser. No. 07/353,847, filed May 17, 1989. The DNA sequence of the Cap/-Polh promoter is given in Table 8 and is set forth in the Sequence Listing as SEQ ID NO:17. The BglII/KpnI fragment of pEV-Tox34 containing the Tox34 coding sequence was inserted in place of the CAT gene in pCap/Polh-CAT (Thiem and Miller (1990) supra), corresponding to pEVvp39/LSXIVCAT. pCap/Polh-Tox34 was cotransfected with vDA26Z (O'Reilly et al. (1990) supra) into Sf cells, and the virus resulting from the homologous recombination between the transplacement plasmid and vDA26Z was designated vCap/Polh-Tox34. That virus was isolated and the correctness of its genetic structure was confirmed by restriction endonuclease analysis.

The effects of vCap/Polh-Tox34 on weight gain were determined by injecting $4 \times 10^5$ plaque-forming units into first day fifth instar T. ni larvae or 2 microliters of tissue culture fluid without virus. Larvae were weighed, injected and placed on a virus-free diet. Larvae infected with vCap/Polh-Tox34 gained significantly less weight and exhibited paralysis earlier than larvae infected with the other recombinant viruses in the comparison set. The maximum weight gained by larvae injected with wild-type AcMNPV was nearly three-fold greater than the maximum weight gained in vCap/Polh-Tox34-infected larvae at one day pi. Over 50% of the test population injected with vCap/Polh Tox34 were paralyzed by day 1 whereas 10% or less of the other test populations were paralyzed or dead by this time post-infection. vCap/Polh-Tox34-infected larvae lost a small amount of weight between one and two days pi, when paralysis of the test population was complete, perhaps due to dehydration of paralyzed larvae. See FIG. 7.

FIG. 7 presents a comparison of the effects of wild-type AcMNPV and recombinant viruses expressing the Tox34 coding sequence on weight gain by infected insect larvae and death or paralysis of infected larvae. At one day pi, weight gain by AcMNPV- and vETL-Tox34-infected larvae were roughly equivalent, while vEV-Tox34, vSp-Tox34 and vCap/Polh-Tox34- infected larvae had lower weight gains.

At two days pi, the weight gains of infected insects in descending order were AcMNPV, uninfected, vETL-Tox34, and pEV-Tox34 and vSp-Tox34 both equivalent, and vCap/Polh-Tox34. At this time all larvae infected with vCap/Polh- Tox34, vEV-Tox34 and vSp-Tox34 were paralyzed or dead while only about 10–15% of larvae infected with AcMNPV or vETL-Tox34 were paralyzed or dead.

By three days pi, uninfected larvae had pupated, and vETL-Tox34-infected larvae had gained significantly less weight than AcMNPV-infected larvae. On the fourth day pi, the remaining infected larvae were either dead or paralyzed.

FIG. 7 demonstrates that vCap/Polh-Tox34 is the most effective insect control agent of those tested in terms of limiting larvae weight gain and in terms of the earliest onset of death or paralysis, which would limit insect feeding. Although expression of the Tox34 coding sequence (See SEQ ID NO:4) in vETL-Tox34 would be expected to be earlier than in the other toxin-producing recombinant viruses, it appears that promoter strength may be less than sufficient for delivering a paralytic dose of toxin to the infected insect early in the infection period. The late/very late hybrid promoter Cap/Polh (SEQ ID NO:17) appears to be significantly stronger, and thus, is the preferred promoter of this set for directing the expression of an insect-specific paralytic neurotoxin in a baculovirus vector.

EXAMPLE 7

Figure 4:
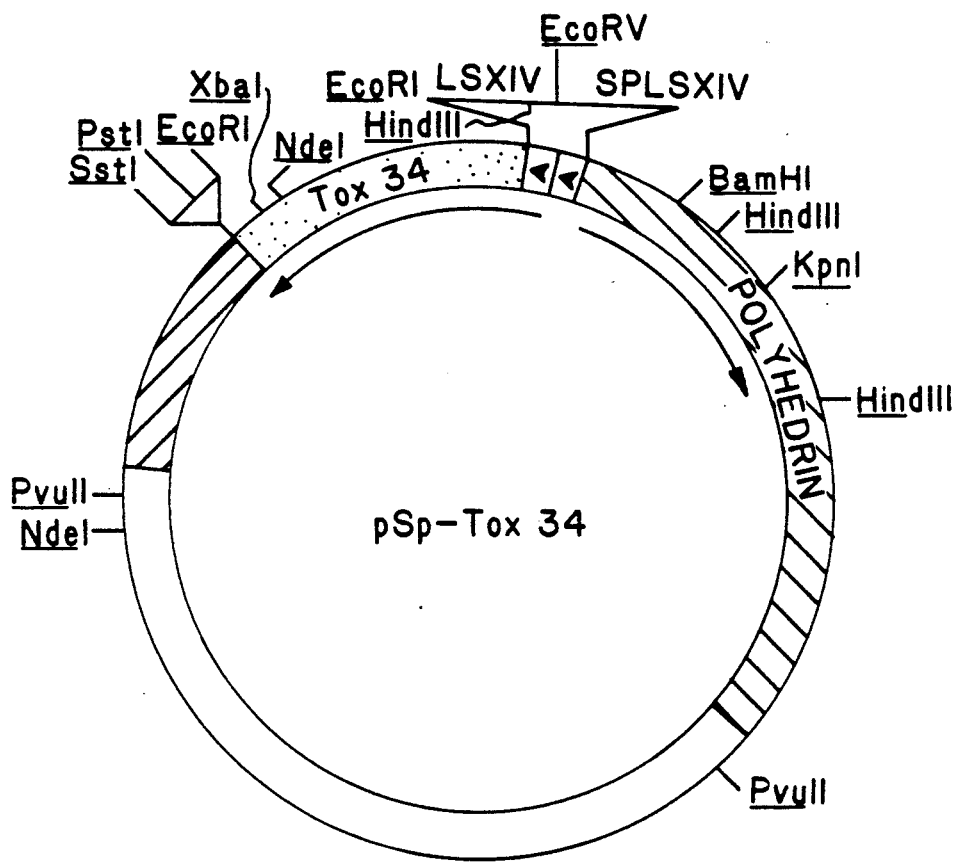
FIG. 4 illustrates transplacement plasmid pSp-Tox34, which was used to construct recombinant virus vSp-Tox34, which expresses the Tox34 coding sequence under the regulatory control of a synthetic hybrid very late promoter (termed SPLSXIV and described in U.S. patent application Ser. No. 353,847, filed May 17, 1989 . pSp-Tox34 contains the entire polyhedrin gene under the control of its own promoter and additional AcMNPV sequences flanking the polyhedrin gene. AcMNPV sequences are shown by slashed lines; vector sequences are shown by an open area. The EcoRI fragment containing the Tox34 coding sequence was inserted into an EcoRI site downstream of the SPLSXIV promoter and in the orientation opposite that of the polyhedrin gene. Gene expression directed by the hybrid promoter is greater than from the polyhedrin promoter. vSp-Tox34 has an occluded phenotype due to the intact polyhedrin gene.
Figure 6:
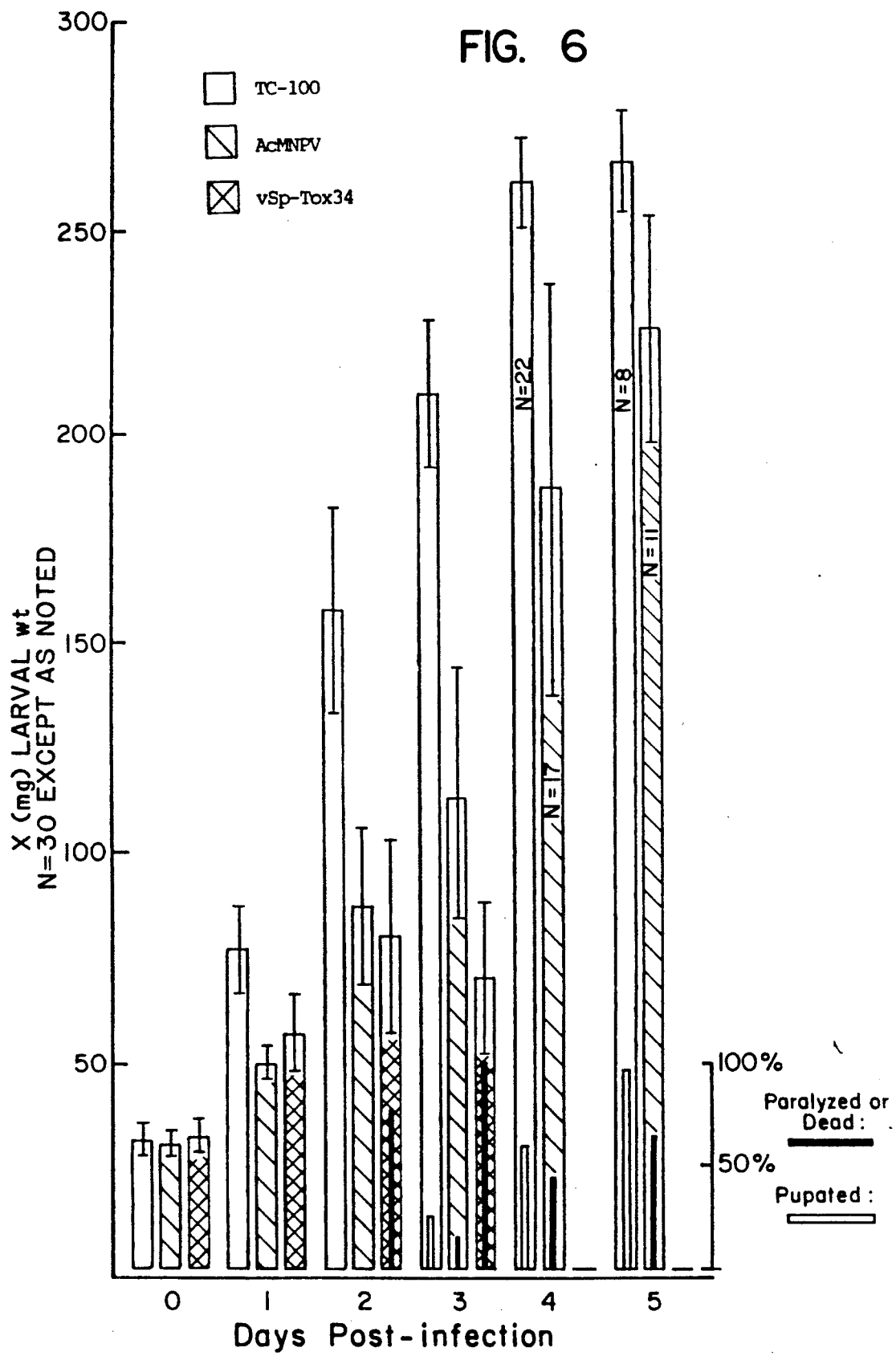
FIG. 6 compares the weight gains of T. ni late fourth and early fifth instar larvae after per os feeding of cul- ture medium (TC-100), and either wild-type AcMNPV or vSp-Tox34 occlusion bodies. The height of the histogram along the y-axis represents the average weight in milligrams of 30 larvae per test virus unless otherwise noted. At later times, average weights were determined only for living insects. The error bars give plus or minus two times the standard error. Generally, the mean plus or minus two standard deviations contains about 95% of the experimental measurements in a standard distribution. Larvae were starved for 24 hrs before they were fed a small cube of diet that had been dipped in a suspension of $2 \times 10^8$ occlusion bodies per ml water. Previous studies have shown that this was an L.D.$_{100}$ dose. After feeding for 24 hrs on infected diet, the larvae were then given uninfected diet and weighed every 24 hrs. Days post-feeding are indicated on the x-axis. Day 0 is the day when the larvae were fed infected diet. Open, slashed and cross-hatched histograms indicate uninfected, and wild-type AcMNPV- and vSp-Tox34-infected larvae, respectively. Bars within each histogram bar show the percentage of larvae that were paralyzed (solid bars) or had pupated (open bars).

Tox34 Expression directed by the SPLSXIV Promoter in an Occlusion-positive Baculovirus The recombinant baculoviruses expressing Tox34 in Example 4 are nonoccluded viruses, and therefore are poorly infectious to insects by an oral route of infection. An occluded baculovirus expressing the Tox34 coding sequence under the regulatory control of a very late promoter and the polyhedrin protein under the control of its own promoter is constructed using the transplacement plasmid pSp-Tox34 shown in FIG. 4. The promoter sequences, designated Sp herein, are called SPLSXIV in U.S. patent application Ser. No. 07/353,847, filed May 17, 1989, and is described therein. The sequence of the Sp promoter is given in Table 9 (See SEQ ID NO:19). pSp-Tox34 is cotransfected into Sf cells together with DNA from an AcMNPV derivative with a beta-galactosidase gene inserted in the polyhedrin gene (vSynVI-gal). This virus has an occlusion-negative phenotype and forms blue plaques when plated on the beta-galactosidase chromogenic substrate 5-bromo-4-chloro-3-indolyl-beta-D-galactopyranoside (X-gal). Other AcNPV derivatives having a deletion of the polyhedrin gene would also be suitable for recombinant virus construction, since the polyhedrin region is replaced by pSp-Tox34 sequences during the allelic replacement step in the construction. The recombinant virus vSp-Tox34, was isolated from the cotransfection progeny as a virus with an occlusion-positive, beta-galactosidase-negative phenotype and expresses TxP-I. 19 of 20 T. ni larvae which were fed vSp-Tox34 during fourth and fifth instars as a contaminant of their diet exhibited paralysis and stopped feeding by 52 hrs from their initial contact with the contaminated diet, whereas larvae fed a diet contaminated with wild-type AcMNPV continued feeding for 5 days (120 hrs) following ingestion of the contaminated diet. Similar results showing weight gains for a test population of 30 larvae are shown in FIG. 6. Larvae fed diet contaminated with vSp-Tox34 showed symptoms of paralysis by 2 days post infection, and greatly reduced weight gains compared to viruses fed wild-type virus. Thus, viruses carrying and expressing an insect-specific paralytic neurotoxin gene such as Tox34 coding sequence have significantly improved pesticidal properties.

EXAMPLE 8

Figure 5:
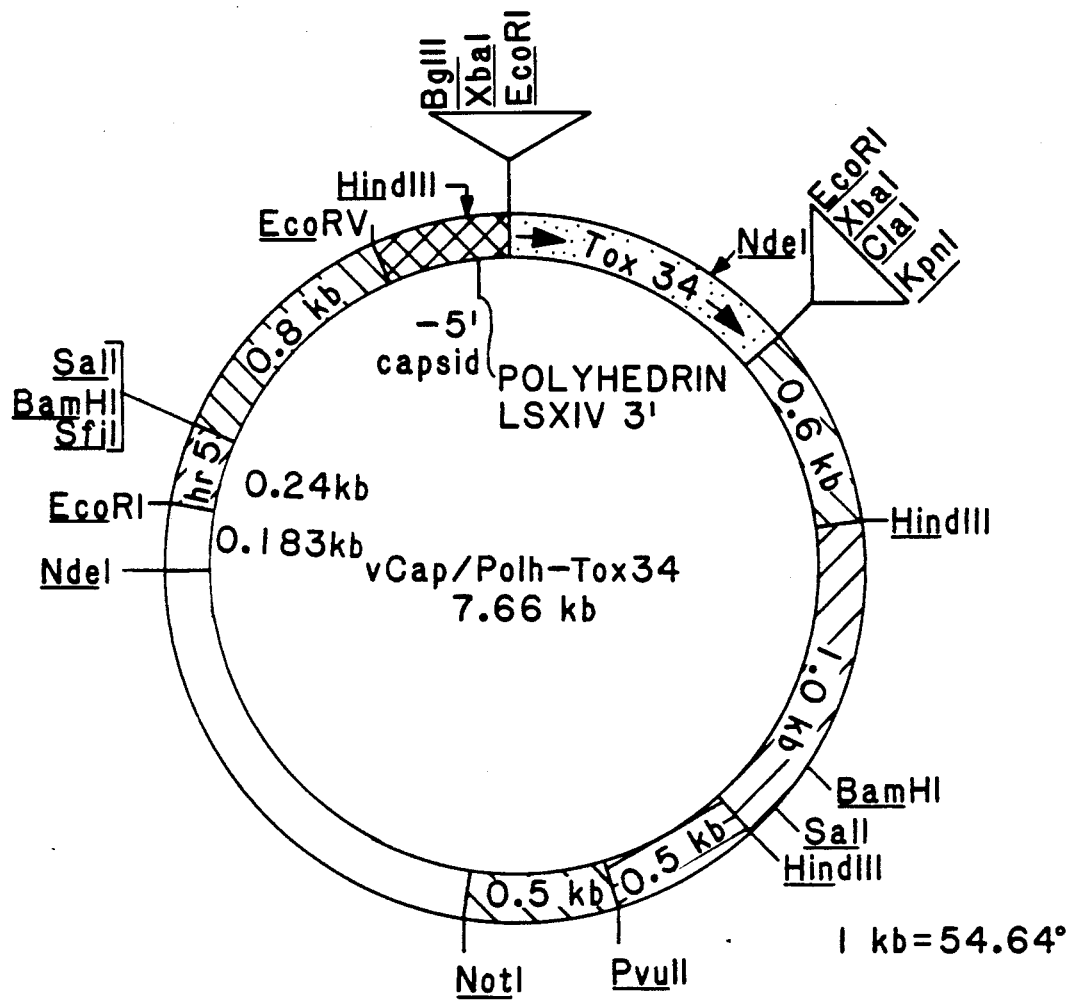
FIG. 5 illustrates the transplacement plasmid pCap/-Polh-Tox34, which is used to construct recombinant virus vCap/Polh-Tox34, which expresses the Tox34 coding sequence under the regulatory control of a Cap/Polh fusion promoter described by Thiem et al. (1990) Gene 91:87–95. The gII/KpnI fragment from pEV-Tox34 containing the Tox34 sequences replaced the CAT gene in pCap/Polh-CAT (Thiem et al. (1990) supra). The direction of the Tox34 coding sequences (stippled region) from the Cap/Polh promoter (cross-hatched region) is shown by the arrowhead. Wild-type viral and pUC8 vector sequences are designated by slashed and open regions, respectively.

Expression of the Tox34 Coding Sequence Directed by the Cap/Polh Promoter in an Occlusion-Positive Baculovirus To make an occlusion-positive baculovirus which expresses the Tox34 coding sequence (See SEQ ID NO:4) under the control of the Cap/Polh promoter, (See SEQ ID NO:17) a plasmid is first constructed which contains between the EcoRI and KpnI sites of the multicloning site of Bluescript plus TM (BSKS+; Stratagene, LaJolla, California) the 4.6 kbp left end of the wild-type AcMNPV EcoRI-I fragment from the EcoRI-I site at 0.0 AcMPV map units to the KpnI site within the polyhedrin gene. This plasmid (pERI-K) is then digested with EcoRV to linearize the plasmid by cutting at the EcoRV site upstream of the polyhedrin gene. The Cap/Polh-Tox34 promoter-gene fusion is removed from pCap/Polh-Tox34 (See FIG. 5) by cutting downstream of Tox34 with KpnI (followed by blunt-ending) and then cutting upstream of the Cap/Polh promoter with EcoRV. The fragment carrying the Cap/Polh-Tox34 fusion is then blunt-end ligated into the EcoRV site of EcoRV-cut pERI-K. The preferred orientation of the toxin gene is counterclockwise with respect to the AcMNPV sequences. The resulting plasmid is designated pCap/Polh-Tox34 VI+.

CapPolh-Tox34 VI+ is used as a transplacement plasmid for allelic replacement with an occlusion-negative AcMNPV derivative with a deletion or substitution mutation in the polyhedrin gene. A suitable deletion mutant is vSynVI-gal as described in Example 7 or a deletion mutant resulting from allelic replacement using plasmid pEVmodXIV.

Recombinant viruses are selected on the basis of their occlusion-positive phenotype and are screened by restriction endonuclease analysis for proper allelic replacement.

Because the modified baculoviruses of Examples 5 and 8 are occluded, they can be incorporated into insecticidally effective, agriculturally acceptable compositions which can be applied to infected crops. Ingestion of such occluded viral particles result in the propagation of those viruses in the field, and spread of insect control agent. Infection will cause insect death and hence, protection of the crops from insect pests. It is understood that a recombinant virus which itself is not capable of directing polyhedrin synthesis may be occluded by another route, e.g., by coinfection with a helper virus which expresses polyhedrin at high levels. Any means known to the art can be employed which would stabilize nonoccluded viruses and thereby increase the effectiveness or efficiency of their use.

EXAMPLE 9

Expression of the Tox21a Coding Sequence in an AcMNPV derivative.

A recombinant AcMNPV capable of expressing the Tox21a coding sequence (See SEQ ID NO:6) under the control of the strong LSXIV promoter is constructed using the following series of steps.

First, the EcoRI cDNA fragment containing Tox21a (See SEQ ID NO:6) is excised from the corresponding lambda ZAPII phage and cloned into the Bluescript plasmid described above to produce pBSK-Tox21a.

It is then desirable to mutagenize the out-of-frame ATG codon (which directs the start of translation with a methionine) at −49, −48, −47 as shown in Table 4 (See SEQ ID NO:6). This site-directed mutagenesis is carried out using polymerase chain reaction technology (Innis et al. (eds.) (1990)*PCR Protocols*, Academic Press, San Diego, California; H. Erlich (ed.) (1989) *PCR Technology*, Stockton Press, New York, New York) and the following primers:

```
              −50          −40          −30          −20
               *            *            *            *
Tox21a    5'-GGCCATGTTAATTTAATAATCTTATTTACAAATTT-3'
Primer 1  5'-GGATCCGTTAATTTAATAATCTTATTTAC-3'
             BamH I I 280          290          300          310
               *            *            *            *
Tox21a    5'-CCT AAAATT GGAACT GT ATGT AGACTTAAAAAAGGA-3'
Primer 2  3'-GGATTTTAACCTT GACATACATCTG-5'
                                      Acc I
```

The Primer 1 and Primer 2 sequences are set forth in the Sequence Listing as SEQ ID NO:2 and SEQ ID NO:3, respectively.

The Primer 1 and Primer 2 sequences are set forth in the Sequence Listing as SEQ ID NO:2 and SEQ ID NO:3, respectively.

PCR is also used to amplify the fragment containing the desired AT to CC mutation. The mutagenesis creates a BamHI site in the upstream region of the Tox21a sequence (See SEQ ID NO:6). The resulting product is digested with BamHI and AccI to release a restriction fragment of about 351 bp, which is then gel-purified.

pBSK-Tox21a is cut with BamHI, which cuts in the vector, and partially cut with AccI which cuts at about nucleotide 300, as in Table 4, in the Tox21a sequence. (See SEQ ID NO:6) This removes the N-terminal portion of the Tox21a sequence from pBSK-Tox21a. The desired vector fragment, which runs about 300–400 bp below single-cut linear pBSK-Tox21a, is gel purified.

The mutated PCR product is then cloned into the purified pBSK-Tox21a vector fragment using standard molecular biological techniques to produce pBSK-mTox21a. The modified Tox21a sequence can then be excised from pBSK-mTox21a by digestion with BamHI and EcoRI, gel purified, and cloned into the transplacement plasmid pEVmodXIV, which is cut with BolII and EcoRI. BolII and BamHI digestions produce compatible 5' overhanging ends, and the modified Tox21a sequence is inserted into pEVmodXIV in the proper orientation relative to the LSXIV promoter. The resulting plasmid pEV-mTox21a is then used for allelic replacement of polyhedrin in wild-type AcMNPV, as described above. The resultant recombinant virus (vEV-Tox21a) will express the Tox21a coding sequence to produce an insect-specific paralytic Tox21a protein.

The skilled artisan will understand the procedural modifications necessary to construct a similar occluded virus or viruses which express Tox21a (See SEQ ID NO:6) under the control of other baculovirus promoters for use in biological insect control agents.

TABLE 1

Toxicity and a Partial List of Host Preferences for Species of Mites in the Genus Pyemotes

| | TOXICITY | | |
|---|---|---|---|
| | INSECTS | HUMANS | HOSTS |
| *ventricosus* group | | | |
| anobii | extreme | (?) | Curculionidae Scolytidae Buprestidae Anobiidae |
| beckeri | extreme | (?) | Lyctidae Scolytidae |
| emarginatus | mild | mild | Cecidomyiidae |
| schwerdtfegeri | extreme | mild | Anobiidae Buprestidae |
| tritici | extreme | extreme | Cucujidae Curculionidae Kalotermitidae Vespidae |
| tuberculatus | (?) | (?) | Anobiidae |
| ventricosus | extreme | extreme | Apoidea Chalcidoidea |
| zwoelferi | extreme | extreme | Cecidomyiidae |
| *scolyti* group | | | |
| dimorphus | mild | none | Scolytidae |
| dryas | mild | none | Scolytidae |
| giganticus | mild | none | Scolytidae |
| parviscolyti | mild | none | Scolytidae |
| scolyti | mild | none | Scolytidae |

*Modified from Cross and Moser (1975) Ann. Entomol. Soc. Am. 68: 723-732.

TABLE 2

DNA and Deduced Amino Acid Sequences of Tox34

```
     1              10              20              30              40              50
     |              |               |               |               |               |
CT TAT TAA TTA ATG AAA ATT TGT ACA TTT TTT ATT CCT TTA TTC AAA ATG AAC TTG TTT TTT
           Met Lys Ile Cys Thr Phe Phe Ile Pro Leu Phe Lys Met Asn Leu Phe Phe 60             70              80              90              100             110
     |              |               |               |               |               |
TTA TTT ATT ATT CCA ACA ATT TTA GCA GTT AAA CCT TTT AGG TCT TTT AAT AAT ATT TCC
Leu Phe Ile Ile Pro Thr Ile Leu Ala Val Lys Pro Phe Arg Ser Phe Asn Asn Ile Ser
```

TABLE 2-continued
DNA and Deduced Amino Acid Sequences of Tox34

```
         120             130             140             150             160             170
          |               |               |               |               |               |
TTA ATT GAT AAT GGC AAT GTC GAA TCT GTA AGA GCA GTA GTT ATT GAT TAT TGT GAT ATT
Leu Ile Asp Asn Gly Asn Val Glu Ser Val Arg Ala Val Val Ile Asp Tyr Cys Asp Ile 180             190             200             210             220             230
          |               |               |               |               |               |
AGA CAT CCA AAT AAT TTA TGT AAA AAA CAT TTT GAA ATC GAT TCA TAT TGG AAT GAT GAT
Arg His Pro Asn Asn Leu Cys Lys Lys His Phe Glu Ile Asp Ser Tyr Trp Asn Asp Asp 240             250             260             270             280             290
          |               |               |               |               |               |
ACG GAT TGT TTT ACA AAT ATT GGA TGC AAA GTA TAT GGA GGA TTT GAT ATT ATT GGT GGT
Thr Asp Cys Phe Thr Asn Ile Gly Cys Lys Val Tyr Gly Gly Phe Asp Ile Ile Gly Gly 300             310             320             330             340             350
          |               |               |               |               |               |
CAT ACC CCT AAA GTT GGA ACT GTA TGT AGA CTT AAA AAA GGA GAA AAT AAA TTT GGA TAT
His Thr Pro Lys Val Gly Thr Val Cys Arg Leu Lys Lys Gly Glu Asn Lys Phe Gly Tyr 360             370             380             390             400             410
          |               |               |               |               |               |
TGT AAT TCA AAG GGA AAT TGC GTT GAA AGA GAT TTT AAA GAA AGT TTT GGA ATA TCT ATA
Cys Asn Ser Lys Gly Asn Cys Val Glu Arg Asp Phe Lys Glu Ser Phe Gly Ile Ser Ile 420             430                             450             460             470
          |               |              440              |               |               |
AAA ATA AAA GGA ATT TCT AAT AAA GGA GAT GAT GAA CCA GCA TGT CCA CAA TAT AAA AAT
Lys Ile Lys Gly Ile Ser Asn Lys Gly Asp Asp Glu Pro Ala Cys Pro Gln Tyr Lys Asn 480             490             500             510             520             530
          |               |               |               |               |               |
ACT TGG ATT AAT TAT GGG AAA TGT AAT GAA CCT TAT TAT TGT GGA ACA AAT CAT GGA TTA
Thr Trp Ile Asn Tyr Gly Lys Cys Asn Glu Pro Tyr Tyr Cys Gly Thr Asn His Gly Leu 540             550             560             570             580             590
          |               |               |               |               |               |
TTT TAT GCA AAC AAA AGA AAA CTC GAT TAC TTT CCC ACA GAC GGT GAA AAA TGT AAT TCA
Phe Tyr Ala Asn Lys Arg Lys Leu Asp Tyr Phe Pro Thr Asp Gly Glu Lys Cys Asn Ser 600             610             620             630             640             650
          |               |               |               |               |               |
AAT AAT ATA CCA TAT GCT GTT TGT TAT TTA GGA AGA TGT CAT ACA ACA GGT GGT TTT TTT
Asn Asn Ile Pro Tyr Ala Val Cys Tyr Leu Gly Arg Cys His Thr Thr Gly Gly Phe Phe 660             670             680             690             700             710
          |               |               |               |               |               |
AGT GAA TTT GGA ACT ATT GTT AAA AAT GTC GAA ATC GTA ACT TTA TCA GAT GGA AAG AAC
Ser Glu Phe Gly Thr Ile Val Lys Asn Val Glu Ile Val Thr Leu Ser Asp Gly Lys Asn 720             730             740             750             760             770
          |               |               |               |               |               |
AGT TCT AGA AGA GGA AAA CAT AAA AAT TTA CCT ACT TCT AAA GTA TTT GAT AGT TAT AGT
Ser Ser Arg Arg Gly Lys His Lys Asn Leu Pro Thr Ser Lys Val Phe Asp Ser Tyr Ser 780             790             800             810             820             830
          |               |               |               |               |               |
ATA TAT GAT ATT GAT CCT AAA AAT TGG AAA ATT GAA GAT GAT GAT AAA GAT GTT ACT GTT
Ile Tyr Asp Ile Asp Pro Lys Asn Trp Lys Ile Glu Asp Asp Asp Lys Asp Val Thr Val 840             850             860             870             880             890
          |               |               |               |               |               |
CAT GAA AAT ACA TTA GAT CCA AAA AGT GAT TCA AGA CTG TGT T AA AAT TTT AAA AAT TTG
His Glu Asn Thr Leu Asp Pro Lys Ser Asp Ser Arg Leu Cys ———

900             910
          |               |
ATT TTT TTA AAT AAA TGT CAA T
```

These sequences are presented as SEQ ID NO:4 and SEQ ID NO:5.
*The underlined amino acids are those identified as the N-terminal amino acids of the purified TxP-I protein.
The first base of the coding sequence of TxP-I is designated 1.

TABLE 3
Comparison of the Empirically Derived and Predicted Amino Acid Compositions of TxP-I

| | EMPIRICAL* | | PREDICTED | |
|---|---|---|---|---|
| | MOLES PERCENT | RESIDUES PER MOLE | MOLES PERCENT | RESIDUES PER MOLE |
| CYS | — | — | 5.56 | 14 |
| CYS** | 7.74 | 18.9 (19) | — | — |
| ASX | 25.67 | 61.2 (61) | 18.26 | 46 |
| THR | 4.47 | 10.6 (11) | 5.56 | 14 |

TABLE 3-continued

Comparison of the Empirically Derived and Predicted Amino Acid Compositions of TxP-I

| | EMPIRICAL* | | PREDICTED | |
|---|---|---|---|---|
| | MOLES PERCENT | RESIDUES PER MOLE | MOLES PERCENT | RESIDUES PER MOLE |
| SER | 6.22 | 14.8 (15) | 6.35 | 16 |
| GLX | 6.29 | 15.0 (15) | 5.16 | 13 |
| PRO | 1.71 | 4.1 (4) | 3.97 | 10 |
| GLY | 11.43 | 27.2 (27) | 9.13 | 23 |
| ALA | 2.16 | 5.1 (5) | 1.59 | 4 |
| ALA** | 2.13 | 5.2 (5) | — | — |
| VAL | 4.09 | 9.8 (10) | 5.95 | 15 |
| MET | 0.18 | 0.4 (1) | 0.00 | 0 |
| ILE | 4.74 | 11.3 (11) | 6.75 | 17 |
| LEU | 3.12 | 7.4 (7) | 3.57 | 9 |
| TYR | 5.41 | 12.9 (13) | 5.56 | 14 |
| PHE | 4.75 | 11.3 (11) | 4.76 | 12 |
| HIS | 2.95 | 7.0 (7) | 2.78 | 7 |
| TRP | — | — | 1.19 | 3 |
| LYS | 11.62 | 27.7 (28) | 10.32 | 26 |
| ARG | 4.89 | 11.6 (12) | 3.57 | 9 |
| TOTAL | 99.65 | 256.3 (257) | 100.00 | 252*** |

*Based on a 27 kDa protein as determined by SDS-PAGE.
**Values obtained from TxP-I oxidized with DMSO/HCl.
***Calculated molecular weight = 28.5 kDa.

TABLE 4

Nucleotide Sequence and Deduced Amino Acid Sequence of Tox21A

```
         -110        -100         -90         -80         -70         -60
           |           |           |           |           |           |
G AAT TCC AAC AAC AGT gcC TTT GGG CGG CCG CAC TGG TCT TAA CTT TTT TCT CTT TTT TAG

-50         -40         -30         -20         -10           1
           |           |           |           |           |           |
    CAG CGG CCA TGA TAA TTT AAT AAT CTT ATT TAC AAA TTT TTT ATT ATT TTA TTC AGA ATG
                                                                                Met 10          20          30          40          50          60
           |           |           |           |           |           |
    AAC TTG TAT TTT TTA TTT TTT ATT TCA ACT ATT TTA GCA GCT AAa CCT TTC AAT TCT TTT
    Asn Leu Tyr Phe Leu Phe Phe Ile Ser Thr Ile Leu Ala Ala Lys Pro Phe Asn Ser Phe 70          80          90         100         110         120
           |           |           |           |           |           |
    AAT AAA ACT TCA TTA ATT GAT GAA GGA GTT GAC AAC GAT GAC GAT ATT GTC TCT AAA AGA
    Asn Lys Thr Ser Leu Ile Asp Glu Gly Val Asp Asn Asp Asp Asp Ile Val Ser Lys Arg 130         140         150         160         170         180
           |           |           |           |           |           |
    GCA GTA GTT ATT GAT TAT TGT GAT ACT AGA CAT CCA AAT AAT TTA TGT AAA AAA TAT TTT
    Ala Val Val Ile Asp Tyr Cys Asp Thr Arg His Pro Asn Asn Leu Cys Lys Lys Tyr Phe 190         200         210         220         230         240
           |           |           |           |           |           |
    GAA ATC GAT TCA TAT TGG AAT GAT GAT ACG GAT TGT TTT ACA AAT ATT GGA TGC AAA GTA
    Glu Ile Asp Ser Tyr Trp Asn Asp Asp Thr Asp Cys Phe Thr Asn Ile Gly Cys Lys Val 250         260         270         280         290         300
           |           |           |           |           |           |
    TAT GGA GGA TTT GAT ATT ATT GGT GGT AAA GCT CCT AAA ATT GGA ACT GTA TGT AGA CTT
    Tyr Gly Gly Phe Asp Ile Ile Gly Gly Lys Ala Pro Lys Ile Gly Thr Val Cys Arg Leu 310         320         330         340         350         360
           |           |           |           |           |           |
    AAA AAA GGA AAA AAT AAA TTT GGA TAT TGT AAT TCA AAA GGA AAT TGC GTT GAA AGA GAT
    Lys Lys Gly Lys Asn Lys Phe Gly Tyr Cys Asn Ser Lys Gly Asn Cys Val Glu Arg Asp 370         380         390         400         410         420
           |           |           |           |           |           |
    TTT ATT GAA AGT TTT GGA GTA TCT ATA AAA ATA AAA GGA ATT TCT CAT AGA GGA GAT GAT
    Phe Ile Glu Ser Phe Gly Val Ser Ile Lys Ile Lys Gly Ile Ser His Arg Gly Asp Asp 430         440         450         460         470         480
           |           |           |           |           |           |
    GAA CCA GCA TGT CCA CTT TAT GAA AAT ACT TGG ATT AAT TAT GGA AAA TGT AAT GAA CCT
    Glu Pro Ala Cys Pro Leu Tyr Glu Asn Thr Trp Ile Asn Tyr Gly Lys Cys Asn Glu Pro 490         500         510         520         530         540
           |           |           |           |           |           |
    TAT CAT TGT GGA ACA AAT TAT GGG TTA TTT TAT GCA AAC AAA AGA AAA CTC AAT TAC TTT
    Tyr His Cys Gly Thr Asn Tyr Gly Leu Phe Tyr Ala Asn Lys Arg Lys Leu Asn Tyr Phe 550         560         570         580         590         600
           |           |           |           |           |           |
    CCT GAT AAC GGT CAA AAA TGT AAT TCA AAA TAT GAA ATA TAC GGT GTA TGT TAT TTA GGA
    Pro Asp Asn Gly Gln Lys Cys Asn Ser Lys Tyr Glu Ile Tyr Gly Val Cys Tyr Leu Gly 610         620         630         640         650         660
           |           |           |           |           |           |
    CGC TGT CAT GGA ACA GGA AAT TTT TCA AAT GGT GAA GTT TTT AGT GAA TTT GGA ACT ATT
    Arg Cys His Gly Thr Gly Asn Phe Ser Asn Gly Glu Val Phe Ser Glu Phe Gly Thr Ile
```

TABLE 4-continued
Nucleotide Sequence and Deduced Amino Acid Sequence of Tox21A

```
     670         680         690         700         710         720
      |           |           |           |           |           |
TTT AAA GAT GTC GAA ATT GTA ACT TTA TCA GAT GGA AAG AAC AGT TCT AAA AGA GGA AAA
Phe Lys Asp Val Glu Ile Val Thr Leu Ser Asp Gly Lys Asn Ser Ser Lys Arg Gly Lys 730         740         750         760         770         780
      |           |           |           |           |           |
CAT AAA AAT TTA CAT GGT TCT AAA GTA TTT GAT AGT AAT GGT ATA TAT GAT ATT GAT CCT
His Lys Asn Leu His Gly Ser Lys Val Phe Asp Ser Asn Gly Ile Tyr Asp Ile Asp Pro 790         800         810         820         830         840
      |           |           |           |           |           |
AAA AAT TGG AAA ATT GAA GAT GAT GAT AAA GAT ATT ACT GTT CAT GAA AAT GCT GGA GAT
Lys Asn Trp Lys Ile Glu Asp Asp Asp Lys Asp Ile Thr Val His Glu Asn Ala Gly Asp 850         860         870         880         890         900
      |           |           |           |           |           |
CCA AAA AGT GAT TCA AGA CGT TGT T A A ATT TTT AAA TAT TTG ATT TTT TTT AAA TAA ATA
Pro Lys Ser Asp Ser Arg Arg Cys — — —

910         920         930         940         950         960
      |           |           |           |           |           |
TAA ATC TAT ATA TTT AAT AAT ATA ATT TCT TTT AAT TTT TAA ATT AGT AAA ATT TCG ATA 970         980         990        1000        1010        1020
      |           |           |           |           |           |
ATT TTA CTT AAT TTT TTA AAT TTA CTA AAT TGA CTA ATT TTA TTA AGA AGT AAC TTC TAA 1030        1040        1050        1060        1070        1080
      |           |           |           |           |           |
AAA TTT GAT TTT TTT TAA AAC AAA TAA TTA TAA ATA TTT TTT AAT TAA ATA AAT TTA ATA 1090        1100        1110        1120
      |           |           |           |
ATT ACA AGA TAA AAA AAA AAA AAA AAA AAG GAA TTC
```

*Bases given in lower case letters are those which were ambiguous positions on the Sequencing gels.
Translation begun with base no. 119
Translation stopped at termination codon (base no. 986)
Sequence printed from base no. 1 to base no. 1240
Sequence numbered beginning with base no. 119
EcoRI recognition sites are underlined

TABLE 5
Comparison of 3'-end Sequences of cDNAs with Homology to Tox34[1]

| | | | | | | |
|---|---|---|---|---|---|---|
| Tox34[2] | +849<br>TCCAAAAAGT | GATTCAAGAC | TGTGTTAAAT | TTTTAAAAAT | TTGATTTTTT | TTAAATAAAT |
| 2AIPT-819 | | | TGTGTTAAAT | TTTTAAAAAT | TTGATTTTTT | TTAAATAAAT |
| 10AIPT-819 | TCCAAAAAGT | GATTCAAGAC | TGTGTTAAAT | TTTTAAAAAT | TTGATTTTTT | TTAAATAAAT |
| 11AIPT-819 | | | | | | TTAAATAAAT |
| 13AIPT-819 | TCCAAAAAGT | GATTCAAGAC | TGTGTTAAAT | TTTTAAAAAT | TTGATTTTTT | TTAAATAAAT |
| 15AII-PT019 | | | | TTTTAAAAAT | TTGATTTTTT | TTAAATAAAT |
| 19DII-PT819 | | | | TTTTAAAAAT | TTGATTTTTT | TTAAATAAAT |
| 21AIIPT-819[3] | TCCAAaAAGT | GATTCAAGAC | GTTGTTAAAT | TTTTAAATAT | TTGATTTTTT | TTAAATAAAT |
| Tox34 | GTCAATCGGA | ATTCGATATC | AAGCTTATCG | ATCC | | |
| 2AIPT-819 | GTCAATCTTT | AAATTATTAA | TAAAATTTGG | GAATTCCTGC | AGCCCGGGGG | ATCCACTAGT |
| 10AIPT-819 | GTCAATCTTT | AAATTATTAA | TAAAATTTGT | AATTAAAGGA | ATTCCTGAAT | ATAAAAAATA |
| 11AIPT-819 | GTCAATCTTT | AAATTATTAA | TAAAATTGCA | TTTTAATATA | TCCTTGTAAA | CCCCAATTTT |
| 13AIPT-819 | GTCAATCTTT | AAATTATTAA | TAAAATTTGT | AATAGCCAGA | CAATATAATC | AAGATCTTTA |
| 15AII-PT819 | GTCAATCTTT | AAATTATTAA | TAAAATTTGT | AACTCTATCC | ATTCTCTCCT | CAACTGTTTT |
| 19DII-PT819 | GTCAATCTTT | AAATTATTAA | TAAAATAATT | TAATTGGGGT | AATTATTTGA | GATTACAAAT |
| 21AIIPT-819 | ATAAATCTAT | ATATTTAATA | ATATAATTTC | TTTTAATTTT | TAAATTAGTA | AAATTTCGAT |
| 2AIPT-819 | TCTAGAGCGG | CCGCCACCGC | GTGGAGCTCA | GCTTTTGTTC | CTTTAGTGAG | GGTTA |
| 10AIPT-819 | GTTTATTTGC | GAAATTAAAA | TTTTTTTTTT | CTATTT | | |

TABLE 5-continued

Comparison of 3'-end Sequences of cDNAs with Homology to Tox34[1]

| | | | | | |
|---|---|---|---|---|---|
| 11AIPT-819 | CACCCC | | | | |
| 13AIPT-819 | GACTTAAGAA | AGCTCTGCTT | TGCTGCTAGA | TGACTTGAAG | TCA |
| 15AII-PT819 | AACAGCAGCC | CGAGCCAAGC | CAAATCATCT | TTGATCTTTT | TTGAACGATC TTATAGCAAA |
| 19DII-PT819 | AATTTTTTAT | TTTAGAACTA | TTTTTTTAGT | TTTTGATAAA | ATACTTTAGG GATAACAGCG |
| 21AIIPT-819 | AATTTTACTT | AATTTTTTAA | ATTTACTAAA | TTGACTAATT | TTATTAAGAA GTAACTTCTA |
| 15AII-PT819 | ATGTTGAATA | CTGTTCTCAA | ACAAAATTTA | GATGAGTCTG | ATCCAGAATT GTTTGATCTAA |
| 19DII-PT819 | TAATTAATTT | ATTTAGATCT | TATATATAAA | TTAGATTGCG | ACCTCGATGT TGGTTTGAAA |
| 21AIIPT-819 | AAAATTTGAT | TTTTTTTAAA | ACAAATAATT | ATAAATATTT | TTTAATTAAA TAAATTTAAT |
| 21AIIPT-819 | AATTACAAGA | TAAAAAAAAA | AAAAAAAAAA | AAAG<u>GAATTC</u> | CTGCAGCCGG GATCACTAGT |
| 21AIIPT-819 | CTAGAGCGCG | CACCCTCAC | | | |

[1]<u>EcoRI</u> recognition sites are underlined.
[2]The Tox34 sequence begins with +849, as in Table 2.
[3]The Tox21a sequence begins with +843, as in Table 4; the clone identification no. is e.g. 21AIIPT-819. The 21AIIPT-819 sequence corresponds to nucleotides 961-1241 of SEQ ID NO: 6, and includes 39 bp of vector sequence downstream of the <u>EcoRI</u> site.
[4]The above sequences are given in the Sequence Listing as follows: 2AIPT-819 as SEQ ID NO:8; 10AIPT-819 as SEQ ID NO:9; 11AIPT-819 as SEQ ID NO:10; 13AIPT-819 as SEQ ID NO:11; 15AII-PT019 as SEQ ID NO:12; 19 DII-PT819 as SEQ ID NO:13; and 21AIIPT-819 as SEQ ID NO:14.

TABLE 6

| | | | | | | |
|---|---|---|---|---|---|---|
| TOX-34 | MKICTFFI | PLFKMNLFFL | FI IPTILAVK | PFRSFNNI SL | IDNG.....N | 43 |
| TOX-21A | | MNLYFL | FFISTILAAK | PFNSFNKTSL | IDEGVDNDDD | 36 |
| TOX-34 | VESVRAVVID | YCDI RHPNNL | CKKHFEIDSY | WNDDTDCFTN | IGCKVYGGFD | 93 |
| TOX-21A | I VSKRAVVID | YCDTRHPNNL | CKKYFEIDSY | WNDDTDCFTN | IGCKVYGGFD | 86 |
| TOX-34 | IIGGHT PKVG | TVCRLKKGEN | KFGYCNSKGN | CVERDFKESF | GI SIKIKGIS | 143 |
| TOX-21A | IIGGKAPKI G | TVCRLKKGKN | KFGYCNSKGN | CVERDFI ESF | GVSIKIKGIS | 136 |
| TOX-34 | NKGDDEPACP | QYKNTWINYG | KCNEPYYCGT | NHGLFYANKR | KLDYFPT DGE | 193 |
| TOX-21A | HRGDDEPACP | LYENTWINYG | KCNEPYHCGT | NYGLFYANKR | KLNYFPDNGQ | 186 |
| TOX-34 | KCNSNNI PYA | VCYLGRCHT T | GGF.....FS | EFGTIVKNVE | IVTLSDGKNS | 238 |
| TOX-21A | KCNSKYEI YG | VCYLGRCHGT | GNFSNGEVFS | EFGTIFKDVE | IVTLSDGKNS | 236 |
| TOX-34 | SRRGKHKNLP | TSKVFDSYS I | YDIDPKNWKI | EDDDKDVTVH | ENTL DPKSDS | 288 |
| TOX-21A | SKRGKHKNLH | GSKVFDSNGI | YDIDPKNWKI | EDDDKDI TVH | ENAGDPKSDS | 286 |
| TOX-34 | RLC | | | | | 291 |
| TOX-21A | RRC | | | | | 289 |

(See SEQ ID NO:5 and SEQ ID NO: 7)

TABLE 7

Nucleotide Matches Between Oligonucleotides Pt-N2, Pt-N1 and Tox34

```
Tox34    D   N   G   N   V   E   S   V   R   A   V   V   I   D   Y
         5'-GAT AAT GGC AAT GTC GAA TCT GTA AGA GCA GTA GTT ATT GAT TAT

Pt-N2                        X   X   X    XXX    X   X   X   X           X
         3'-CTA TTA CCG TTA CAC CTC AGG CAC GCG CGG CAC CAC TAG CTA ATG
              G   G       G                                           G

Pt-N1    3'-CTI TTI CCN TTI CAN CT-5'

Tox34    C   D   I   R   H   P
         TGT GAT ATT AGA CAT CC-3'
```

TABLE 7-continued

Nucleotide Matches Between Oligonucleotides Pt-N2, Pt-N1 and Tox34

Pt-N2  XX        X X X    X
     AGG CTA TAG GCG GTG CG-5'
           G

The top line of letters represents the single letter amino acid designation for the first 21 amino acid residues of the N-terminus of Tox34. The second line, labeled Tox34, gives the 5'-3' nucleotide sequence of the Tox34 gene, and the fourth and fifth lines give the 3'-5' nucleotide sequence and degeneracy respectively of Pt-N2. The X's between the Tox34 and Pt-N2 nucleotide sequences designate the 17 mismatched bases. The nucleotide sequence of Pt-N1 is also given below Pt-N2. Deoxyinosine is indicated by I, and N indicates completely degenerate positions.
The nucleotide sequences of Primer Pt-N2 and Primer Pt-N1 are given in the Sequence Listing as SEQ ID NO:15 and SEQ ID NO:16, respectively.

TABLE 8

Sequence of the Cap\polh promoter/Tox 34 fusion within the EcoRV-KpnI region of the AcMNPV polyhedrin gene region EcoRV
G ATA TCT TGT TCG CCA TCG TGG AAT CAA ATA GAT CAA TGT CAC TTT TCG AAA AAT ATA CAT

GTT CAA ATT TGA TTT CAA TTT TAT CGT GTT GGT AAA CGT ACA CTT TAA TTA TTT TAC TCA

AGT TGT GCG AAA GAG TCT TGT AAG GCA GTT TGA TTT CTT TGC TTT CTC TCC ACA CCA ACG

GCA CCA ACG CGT TGG TAT CTT TAG GCC AAT AAA CAA ATT TTT TGT GTT TGG AAT TAG TCT

TTT TCA CGC TTG ATA TTA TGT TAT TGC AAG CGC TCT GAA TAG GTA TAC GAG TGC GAA AGC

CGT TTT CGT CGT ACA AAT CGA AAT ATT GTT GTG CCA GCG AAT AAT TAG GAA CAA TAT AAG

AAT TTA AAA CCA AGC TTG GCG CAA ATA AAT AAG TAT TTT ACT GTT TTC GTA ACA GTT TTG

TAA TAA AAA AAC CTA TAA ATA GAT CTC GAG AAT TC . . Tox34 cDNA . . . G AAT TCT AGA TCG ATG GTA CC
                         BglII          EcoRI                              EcoRI                 KpnI

The nucleotide sequence of the EcoRV to EcoRI fragment comprising the cap/polh promoter is given in the Sequence Listing as SEQ ID NO:18. The AcMNPV nucleotide sequence downstream of the EcoRI site is given in the Sequence Listing as SEQ ID NO:17.

TABLE 9

Sequence of the SpLSXIV promoter fused into the EcoRV site at -92 upstream of the AcMNPV polyhedrin open reading frame EcoRV/SmaI    HindIII
5'GAT/GGGCCAAGCTTGGCGTTATTGAATAAGAATTTAAAAATCAATC EcoRV
                                      ATTTGTATACTGTAAATTACATACTGTTTTATTTAACAATAGATATC ATGGAGATAATTAAAATGCCAAGCTTGGCGCAAATAAATAAGTATT
                            Hind III linker TTACTGTTTTCGTAACAGTTTTGTAATAAAAAAACCTATAAATAGATCA
                                                                                                                   EcoRV/BglII TCGAATTC . . . tox34 insert . . . GAATTCTCGAGCTGCAGATCTGTCGACCCGGGAATAAAGAGCTCCA/ATC . .
EcoRI                       EcoRI                                                                                                            /EcoRV The nucleotide sequence of the SpLSXIV promoter region (EcoRV to EcoRI region) is given in the Sequence Listing as SEQ ID NO:20.
The AcMPV nucleotide sequence downstream of the EcoRI cloning site is given in the Sequence Listing as SEQ ID NO:19.

We claim

1. An isolated and purified recombinant DNA molecule comprising a first nucleic acid sequence and a second nucleic acid sequence, said first nucleic acid sequence encoding an insect-specific paralytic neurotoxin of an insect-predacious mite, wherein said nucleic acid sequence has at least 70% nucleotide sequence homology to the nucleotide sequence encoding an insect-specific paralytic neurotoxin as shown in SEQ ID NO:4 from nucleotide 129 to nucleotide 884, and said second nucleic acid sequence being selected from the group consisting of a virus vector, a bacteriophage vector and a plasmid vector, wherein said first nucleic acid is covalencly linked to said second nucleic acid sequence.

2. The isolated and purified recombinant DNA molecule of claim 1 wherein said insect-predacious mite is of the genus Pyemotes.

3. The isolated and purified recombinant DNA molecule of claim 2 wherein said insect-predacious mite is of the species *Pyemotes tritici*.

4. The isolated and purified recombinant DNA molecule of claim 1 wherein the encoded insect-specific paralytic neurotoxin comprises an amino acid sequence as in SEQ ID NO:5, from an aspartate at amino acid 1 to a cysteine at amino acid 252.

5. The isolated and purified recombinant DNA molecule of claim 4 wherein said nucleic acid sequence is as in SEQ ID NO:4, from nucleotide 129 to nucleotide 884.

6. An isolated and purified recombinant DNA molecule comprising a first nucleic acid sequence and a second nucleic acid sequence, said first nucleic acid sequence encoding an insect-specific paralytic neurotoxin of an insect-predacious mite, said neurotoxin having an amino acid sequence with at least about 83% amino acid sequence similarity with an amino acid sequence of an insect-specific paralytic neurotoxin of an insect-predacious mite as in SEQ ID NO:7, and said nucleic acid sequence being selected from the group consisting of a virus vector, a bacteriophage vector and a plasmid vector.

7. An isolated and purified recombinant DNA molecule comprising a first nucleic acid sequence and a second nucleic acid sequence, said first nucleic acid sequence encoding an insect-specific paralytic neurotoxin of an insect-predacious mite, said nucleic acid sequence having at least about 70% nucleic acid sequence homology with a nucleic acid sequence as in SEQ ID NO:6 from nucleotide 119 to nucleotide 985, and said second nucleic acid sequence being selected from the group consisting of a virus vector, a bacteriophage vector and a plasmid vector.

8. The isolated and purified recombinant DNA molecule of claim 7 wherein said gene has said first nucleic acid sequence encoding the insect-specific paralytic neurotoxin of an insect-predacious mite as in SEQ ID NO:6 from nucleotide 119 to nucleotide 985.

9. The isolated and purified recombinant DNA molecule of claim 7 wherein said nucleic acid sequence encodes an insect-specific paralytic neurotoxin having an amino acid sequence as in SEQ ID NO:7.

10. A baculovirus insect control agent which has been genetically engineered to contain and express a nucleic acid sequence encoding an insect-specific paralytic neurotoxin of an insect predacious mite, said neurotoxin having at least 83% amino acid sequence identity with an amino acid sequence as in SEQ ID NO;5 from an aspartate at amino acid 1 to a cysteine at amino acid 252.

11. An isolated and purified recombinant DNA molecule comprising a first nucleic acid sequence and a second nucleic acid sequence, said first nucleic acid sequence encoding an insect-specific paralytic neurotoxin of an insect-predacious mite, wherein said encoded neurotoxin has at least about 83% sequence identity with an amino acid sequence as shown in SEQ ID NO:5 from an aspartate at amino acid 1 to a cysteine at amino acid 252, and a second nucleic acid sequence, said second nucleic acid sequence selected from the group of consisting of a virus vector, a bacteriophage vector and a plasmid vector, wherein said first nucleic acid sequence is covalently jointed to said second nucleic acid sequence.

12. The isolated and purified recombinant DNA molecule of claim 11 wherein the encoded insect-specific paralytic neurotoxin comprises an amino acid sequence as in SEQ ID NO:7.

13. A baculovirus insect control agent which has been genetically engineered to contain and express a nucleic acid sequence encoding an insect-specific paralytic neurotoxin of an insect predacious mite, said nucleic acid sequence having at least 70% nucleic acid sequence homology with a nucleic acid sequence as in SEQ ID NQ:4, from nucleotide 129 to nucleotide 884.

14. The baculovirus insect control agent of claim 13 wherein said insect-predacious mite is of the genus Pyemotes.

15. The baculovirus insect control agent of claim 14 wherein said insect-predacious mite is of the species *Pyemotes tritici*.

16. The baculovirus insect control agent of claim 13 wherein said nucleic acid sequence encodes an insect-specific paralytic neurotoxin having an amino acid sequence as in SEQ ID NO:5, from an aspartate at amino acid 1 to a cysteine at amino acid 252.

17. The baculovirus insect control agent of claim 16 wherein said nucleic acid sequence has a sequence as in SEQ ID NO:4 from nucleotide 129 to nucleotide 884.

18. The baculovirus insect control of claim 13 wherein said baculovirus is a nuclear polyhedrosis virus derivative.

19. The baculovirus insect control agent of claim 18 wherein said baculovirus is an AcMNPV derivative.

20. The baculovirus insect control agent of claim 19 wherein said AcMNPV derivative expresses said neurotoxin under the regulatory control of a promoter which acts very late during infection.

21. The baculovirus insect control agent of claim 20 which is vEV-Tox34.

22. The baculovirus insect control agent of claim 19 wherein said AcMNPV derivative expresses said neurotoxin under the regulatory control of a promoter expressed early in virus infection.

23. The baculovirus insect control agent of claim 22 which is vETL-Tox34.

24. The baculovirus insect control agent of claim 19 wherein said neurotoxin is expressed under the regulatory control of a synthetic promoter.

25. The baculovirus insect control agent of claim 24 which is vSp-Tox34.

26. The baculovirus insect control agent of claim 19 wherein said neurotoxin is expressed under the regulatory control of a hybrid promoter.

27. The baculovirus insect control agent of claim 26 which is vCap/Pol-Tox34.

28. A baculovirus insect control agent which has been genetically engineered to contain and express a nucleic acid sequence encoding an insect-specific paralytic neurotoxin of an insect-predacious mite, where in said encoded neurotoxin has at least about 83% amino acid sequence identity with an amino acid sequence as in SEQ ID NO:7.

29. A baculovirus insect control agent which has been genetically engineered to contain and express a nucleic acid sequence encoding an insect-specific paralytic neurotoxin of an insect-predacious mite, wherein said nucleic acid sequence has at least about 70% nucleic acid sequence homology with a nucleic acid sequence as in SEQ ID NO:6 from nucleotide 119 to nucleotide 985.

30. The baculovirus insect control agent of claim 29 wherein said nucleic acid sequence encodes an insect-specific paralytic neurotoxin having an amino acid sequence as in SEQ ID NO:7.

31. The baculovirus insect control agent of claim 30 wherein said nucleic acid sequence is as in SEQ ID NO:6 from nucleotide 119 to nucleotide 985.

32. An insect-toxin composition comprising an amount of a baculovirus effective for causing a toxic effect on a target insect, which baculovirus has been genetically modified to express a nucleic acid sequence encoding an insect-specific paralytic neurotoxin of an insect-predacious mite, wherein said nucleic acid sequence has at least about 70% nucleotide sequence homology to a nucleic acid sequence as in SEQ ID NO:4 from nucleotide 129 to nucleotide 884, said composition further comprising an agriculturally acceptable carrier.

33. The insect-toxic composition of claim 32 wherein said nucleic acid sequence is as in SEQ ID NO:4 from nucleotide 129 to nucleotide 884.

34. The insect-toxic composition of claim 32 wherein said baculovirus is an AcMNPV derivative.

35. The insect toxic composition of claim 34 wherein said AcMNPV derivative expresses said gene under the regulatory control of a promoter active very late in infection.

36. The insect-toxic composition of claim 35 wherein said AcMNPV derivative is vEV-Tox34.

37. The insect toxic composition of claim 34 wherein said AcMNPV derivative expresses said gene under the regulatory control of a promoter expressed early during viral infection.

38. The insect-toxic composition of claim 37 wherein said AcMNPV derivative is vETL-Tox34.

39. The insect toxic composition of claim 34 wherein said AcMNPV derivative expresses said gene under the regulatory control of a hybrid promoter.

40. The insect-toxic composition of claim 39 wherein said AcMNPV derivative is one of vSp-Tox34 and vCap/Polh-Tox34.

41. The insect-toxic composition of claim 34 wherein said AcMnPV derivative is vSp-Tox34.

42. An insect-toxic composition comprising an amount of a baculovirus effective for causing a toxic effect on a target insect, which baculovirus has been genetically modified to express a nucleic acid sequence encoding an insect-specific paralytic neurotoxin of an insect-predacious mite, wherein said encoded neurotoxin has at least about 83% amino acid sequence identity with an amino acid sequence as in SEQ ID NO:5 from amino acid 1 to amino acid 252, said composition further comprising an agriculturally acceptable carrier.

43. The insect-toxic composition of claim 42, wherein said encoded neurotoxin has an amino acid sequence as in SEQ ID NO:5 from an aspartate at amino acid 1 to a cysteine at amino acid 252.

44. The insect-toxic composition of claim 43 wherein said neurotoxin is encoded by a nucleic acid sequence as in SEQ ID NO:4 from nucleotide 129 to nucleotide 884.

45. An insect-toxic composition comprising an amount of a baculovirus effective for causing a toxic effect on a target insect, which baculovirus has been genetically modified to express an insect-specific paralytic neurotoxin of an insect-predacious mite, wherein said neurotoxin has at least about 83% amino acid sequence identity with an amino acid sequence as in SEQ ID NO:7, said composition further comprising an agriculturally acceptable carrier.

46. An insect-toxic composition comprising an amount of a baculovirus effective for causing a toxic effect on a target insect, which baculovirus has been genetically modified to express a nucleic acid sequence encoding an insect-specific paralytic neurotoxin of an insect-predacious mite, wherein nucleic acid sequence has at least about 70% nucleic acid sequence homology to a nucleic acid sequence as in SEQ ID NO:6 from nucleotide 119 to nucleotide 985, said composition further comprising an agriculturally acceptable carrier.

47. The insect toxic composition of claim 46 wherein said neurotoxin has an amino acid sequence as in SEQ ID NO:7.

48. The insect-toxic composition of claim 46 wherein said nucleic acid sequence is as given in SEQ ID NO:6 from nucleotide 119 to nucleotide 985.

49. A method for the control of insect pests comprising the step of applying an insect-toxic amount of the insect composition of claim 32 to a habitat of said insect pests.

50. The method of claim 49 wherein said insect habitat is a plant.

51. A method for the control of insect pests comprising the step of distributing a bait comprising the an insect-toxic amount of the insect-toxic composition of claim 45.

52. A method for the production of an insect-specific paralytic neurotoxin of an insect-predacious mite in a host cell, wherein a nucleic acid sequence encoding said neurotoxin has at least about 70% nucleotide sequence homology with a nucleotide sequence as given in SEQ ID NO:4, from nucleotide 129 to nucleotide 884, said method comprising the steps of:

(a) construction a recombinant DNA molecule, which molecule comprises a vector portion capable of introduction into and replication in said host cell, a promoter which functions in said host cells, and a coding sequence for said insect-specific paralytic neurotoxin of an insect-predacious mite, said coding sequence being expressible in said host cell, said coding sequence and said promoter being position in said molecule such that said coding sequence is expressed under the regulatory control of said promoter in said host cell;

(b) introducing said recombinant DNA molecule into said host cell, thereby producing a genetically altered host cell; and (c) culturing said genetically altered host cell such that said coding sequence is expressed and said neurotoxin is produced.

53. The method of claim 52 further comprising the steps of recovering and purifying said neurotoxin after the culturing step.

54. The method of claim 52 wherein said vector portion is derived from a baculovirus.

55. The method of claim 54 wherein said baculovirus is a nuclear polyhedrosis virus.

56. The method of claim 55 wherein said nuclear polyhedrosis virus is AcMNPV.

57. The method of claim 52 wherein said insect-predacious mite is of the genus Pyemotes.

58. The method of claim 57 wherein said insect-predacious mite is of the species *Pyemotes tritici*.

59. The method of claim 52 wherein said encoded neurotoxin has an amino acid sequence as in SEQ ID NO:5 from an aspartate at amino acid 1 to a cysteine at amino acid 252.

60. The method of claim 52 wherein said neurotoxin is encoded by a nucleic acid sequence as in SEQ ID NO:6 from nucleotide 119 to nucleotide 985.

61. The method of claim 52 wherein said neurotoxin has an amino acid sequence as in SEQ ID NO:7.

* * * * *

UNITED STATES PATENT AND TRADEMARK OFFICE
CERTIFICATE OF CORRECTION

PATENT NO. : 5,266,317
DATED : November 30, 1993
INVENTOR(S) : Tomalski, et, al.

It is certified that error appears in the above-indentified patent and that said Letters Patent is hereby corrected as shown below:

At column 3, line 3, please rewrite "epizoptic" as --epizootic--. At column 3, line 52, please rewrite "p," as --*supra*,--. At column 4, line 43, please rewrite "5,180,580" as --5,180,581--. At column 5, line 32, please rewrite "*thurinoiensis*" as --*thuringiensis*--. At column 7, line 7, please rewrite "of" as --orf--. At column 9, line 59, please rewrite "gII" as --BglII--. At column 10, line 23, please delete "pi". At column 11, line 23, please rewrite "*P. emeroinatus, P. schwerdtfeoeri*" as --*P. emerginatus, P.schwerdtfegeri*--. In column 13, line 14, please rewrite "Grner" as --Gröner--. In column 21, line 11, please rewrite "sura" as --supra--. In column 21, line 42, please rewrite "5,180,580" as --5,180,581--. In column 22, line 18, please rewrite "BlII" as --BglII--. In column 24, line 42, please rewrite "CapPolh-" as --pCapPolh---. In column 25, line 58, please rewrite "BolII" as --BglII--. In column 26, line 1, please rewrite "BolII" as --BglII--. In Table 2, column 28, nucleotide no. 878, please replace "A" with --T--. In column 55, line 33, please rewrite "insect-toxin" as --insect-toxic--.

Signed and Sealed this

Nineteenth Day of July, 1994

Attest:

BRUCE LEHMAN

*Attesting Officer*     Commissioner of Patents and Trademarks